US010980679B2

(12) United States Patent
Chatterjee et al.

(10) Patent No.: US 10,980,679 B2
(45) Date of Patent: Apr. 20, 2021

(54) ABSORBENT ARTICLE HAVING WAIST GASKETING ELEMENT

(71) Applicant: The Procter & Gamble Company, Cincinnati, OH (US)

(72) Inventors: Kumardipti Chatterjee, Indian Hill, OH (US); Jeromy Thomas Raycheck, South Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 949 days.

(21) Appl. No.: 15/600,028

(22) Filed: May 19, 2017

(65) Prior Publication Data

US 2017/0333262 A1 Nov. 23, 2017

Related U.S. Application Data

(60) Provisional application No. 62/339,109, filed on May 20, 2016.

(51) Int. Cl.
*A61F 13/49* (2006.01)
*A61F 13/15* (2006.01)
(Continued)

(52) U.S. Cl.
CPC .......... *A61F 13/4902* (2013.01); *A61F 13/15* (2013.01); *A61F 13/49* (2013.01);
(Continued)

(58) Field of Classification Search
CPC ................ A61F 13/15; A61F 13/49473; A61F 2013/530598; A61F 13/49466;
(Continued)

(56) References Cited

U.S. PATENT DOCUMENTS 5,151,092 A  9/1992 Buell et al.
5,827,259 A  10/1998 Laux et al.
(Continued)

FOREIGN PATENT DOCUMENTS

CN  203060062  7/2013
CN  105142589 A  12/2015
(Continued)

OTHER PUBLICATIONS

International Search Report, PCT/US2017/033533, dated Jul. 19, 2017, 15 pages.

*Primary Examiner* — Michele M Kidwell
(74) *Attorney, Agent, or Firm* — Daniel S. Albrecht; Wednesday G. Shipp

(57) ABSTRACT

An absorbent article for wearing about the lower torso of a wearer includes a first waist region having a first waist edge, a second waist region having a second waist edge, and a crotch region disposed between the first and second waist regions. The article further includes a first longitudinal edge, a second longitudinal edge, and a chassis having a topsheet, a backsheet, and an absorbent core disposed between the topsheet and backsheet. A waist gasketing element is joined to the chassis and disposed in one of the first waist region or the second waist region. The waist gasketing element has a top layer and a bottom layer, an inboard lateral edge and an outboard lateral edge, and first area, A1. The top layer is bonded to the bottom layer in a closure bond region by a closure bonding technique. The closure bond region has an aggregate closure bond area, BA, which is at least about 10% of the first area, A1.

21 Claims, 8 Drawing Sheets

(51) Int. Cl.
*A61F 13/494* (2006.01)
*A61F 13/53* (2006.01)
*A61F 13/514* (2006.01)

(52) U.S. Cl.
CPC .. *A61F 13/49019* (2013.01); *A61F 13/49473* (2013.01); *A61F 13/53* (2013.01); *A61F 2013/51409* (2013.01); *A61F 2013/51452* (2013.01); *A61F 2013/530598* (2013.01)

(58) Field of Classification Search
CPC ........ A61F 13/4948; A61F 2013/49493; A61F 13/49; A61F 13/49019; A61F 13/4902; A61F 13/53; A61F 2013/51409; A61F 2013/51452
See application file for complete search history.

(56) References Cited

U.S. PATENT DOCUMENTS

| | | | |
|---|---|---|---|
| 5,833,677 A * | 11/1998 | Sauer | A61F 13/49466 604/369 |
| 5,904,675 A * | 5/1999 | Laux | A61F 13/49009 604/385.29 |
| 5,993,433 A | 11/1999 | St. Louis et al. | |
| 6,083,212 A | 7/2000 | Kumasaka | |
| 7,879,017 B1 | 2/2011 | Tabata et al. | |
| 9,023,007 B2 | 5/2015 | Hashino et al. | |
| 10,159,610 B2 * | 12/2018 | Barnes | A61F 13/49011 |
| 10,398,608 B2 * | 9/2019 | Chatterjee | A61F 13/49413 |
| 10,406,040 B2 * | 9/2019 | Chatterjee | A61F 13/49 |
| 10,470,943 B2 * | 11/2019 | Jang | A61F 13/49466 |
| 10,485,710 B2 * | 11/2019 | Surushe | A61F 13/4942 |
| 10,524,962 B2 * | 1/2020 | Raycheck | A61F 13/49011 |
| 10,524,963 B2 * | 1/2020 | Surushe | A61F 13/49011 |
| 10,531,991 B2 * | 1/2020 | Raycheck | A61F 13/495 |
| 10,588,791 B2 * | 3/2020 | Raycheck | A61F 13/496 |
| 2002/0173768 A1 * | 11/2002 | Elsberg | A61F 13/49012 604/391 |
| 2004/0122413 A1 | 6/2004 | Roessler et al. | |
| 2004/0243085 A1 | 12/2004 | Veith et al. | |
| 2007/0293832 A1 * | 12/2007 | Wood | A61F 13/49011 604/385.01 |
| 2008/0147025 A1 * | 6/2008 | Van Gompel | A61F 13/495 604/358 |
| 2011/0046586 A1 | 2/2011 | Kawakami et al. | |
| 2012/0277703 A1 * | 11/2012 | Rhein | A61F 13/49007 604/369 |
| 2014/0000795 A1 | 1/2014 | Hamilton et al. | |
| 2016/0106601 A1 | 4/2016 | Kobayashi et al. | |
| 2017/0000656 A1 * | 1/2017 | Chatterjee | A61F 13/49 |
| 2017/0246055 A1 * | 8/2017 | Barnes | A61F 13/15747 |
| 2017/0333261 A1 * | 11/2017 | Chatterjee | A61F 13/49012 |

FOREIGN PATENT DOCUMENTS

| | | |
|---|---|---|
| EP | 0865780 | 9/1998 |
| EP | 1621168 | 2/2006 |
| EP | 2135733 | 12/2009 |
| JP | 11137601 | 5/1999 |
| JP | 2000107223 | 4/2000 |
| JP | 2004229857 | 8/2004 |
| JP | 2008136793 | 6/2008 |
| JP | 2014221097 | 11/2014 |
| WO | WO 2000/07534 | 2/2000 |
| WO | WO 2007/37390 | 4/2007 |
| WO | WO 2012/73901 | 6/2012 |
| WO | WO 2016/068963 | 5/2016 |

* cited by examiner

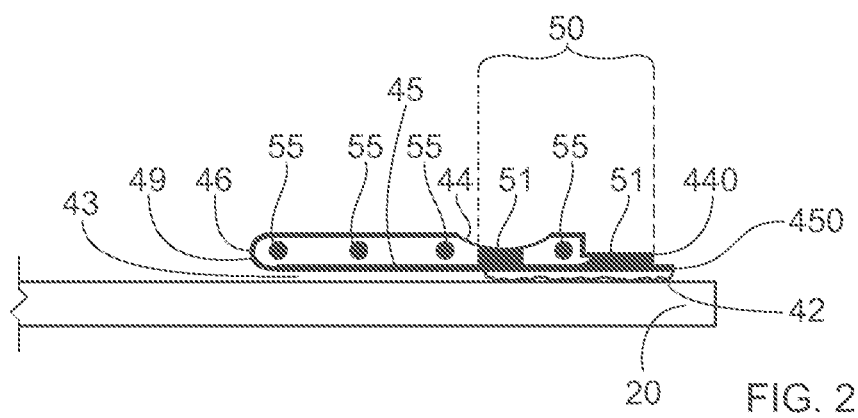
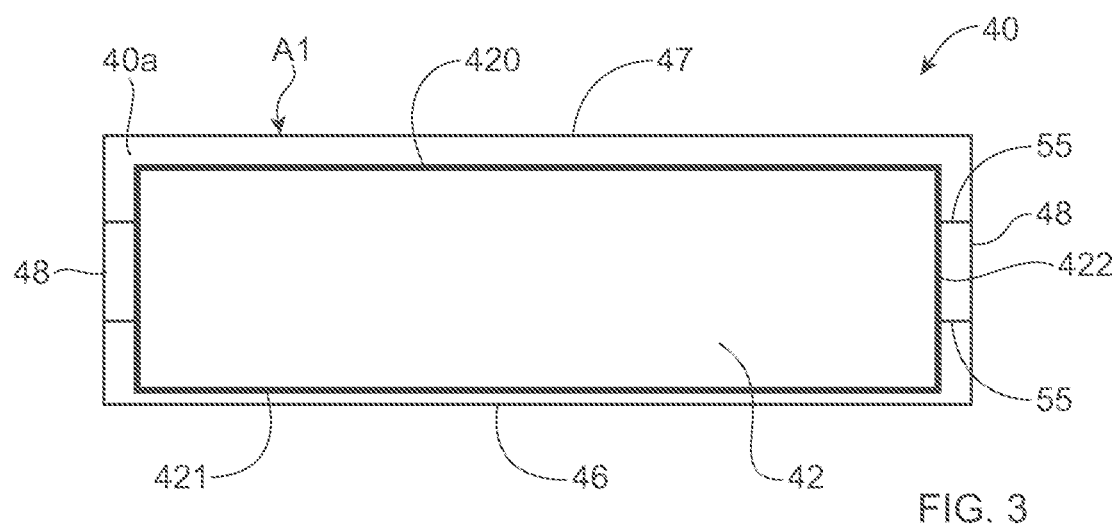

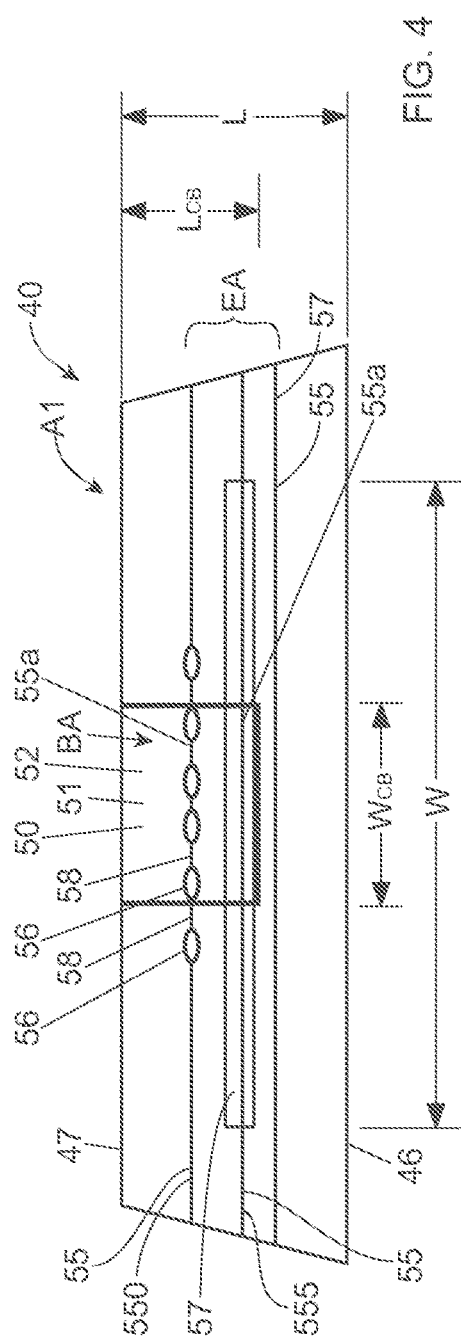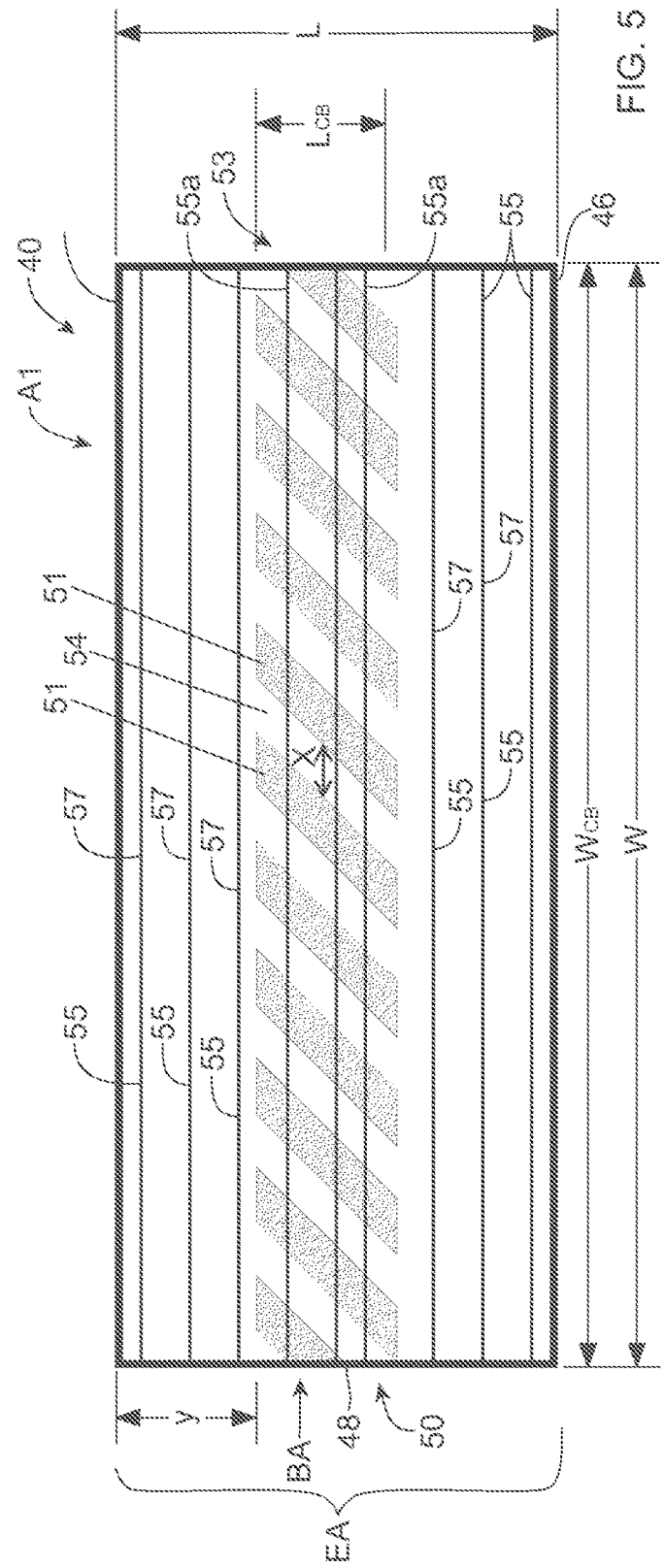

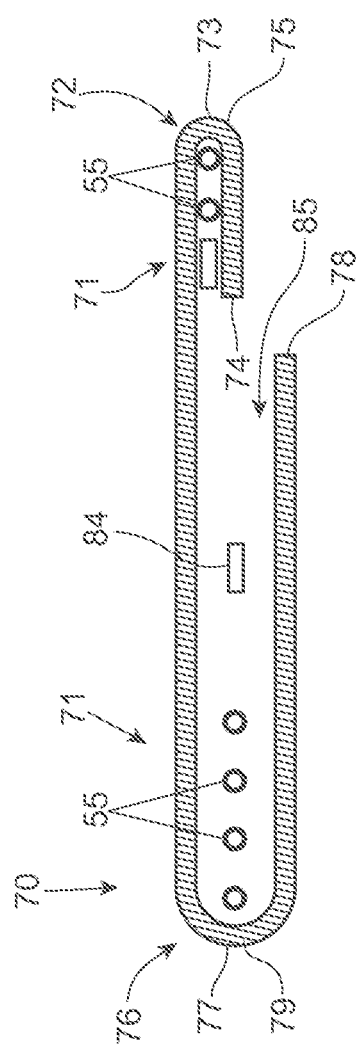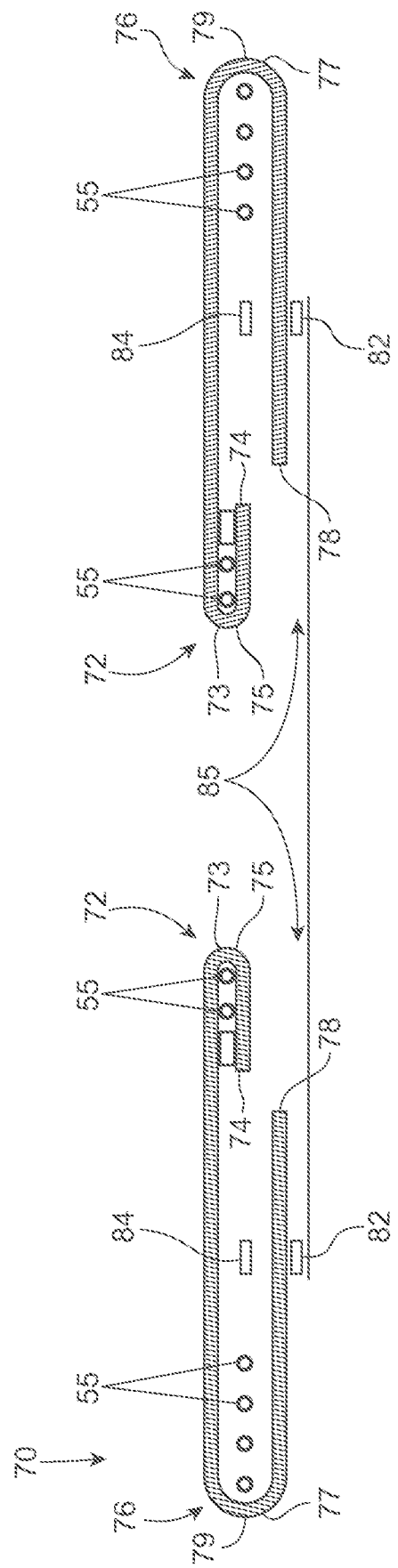

ABSORBENT ARTICLE HAVING WAIST GASKETING ELEMENT

FIELD OF THE INVENTION

This invention relates to absorbent articles (e.g., diapers, adult incontinence articles) having waist gasketing elements, in particular absorbent articles having elasticized waist gasketing elements.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Manufacturers often use elasticized areas, such as elasticized waistbands, within the article to help achieve a snug fit. Ideally, elastics are placed close to a material edge within an article in order to ensure better conformity to the wearer's body. However, such placement increases the risk of an elastic becoming exposed outside of the product during handling or use of the product. Such exposure could lead to safety risks (e.g., wearers eating exposed elastics, snapping or other injury caused by exposed elastics) as well as performance failures because the unsecured elastics will not perform as desired. Not only does the proximity of elastics to edges increase the potential for exposure, but manufacturing processes may also increase this risk. Indeed, when a waistband is applied to a continuous web of chassis material which is subsequently cut into individual articles, one of the final articles may be cut in such a way that an elastic is released. Typically, a knife or other cutting equipment is used to separate articles. Because the blade is parallel to the laterally extending waist elastics, manufacturing variability could lead to a cut immediately along the edge of an elastic and/or a cut across the elastic. Further, when separating a web of elasticized waistbands into individual waistbands, the risk for exposing an elastic is even greater, considering the precision required for cutting between two adjacent elastics. While providing a larger distance between elastics would reduce the risk of exposing the elastics in this situation, doing so would result in elastics being further away from the waist edge of the individual products. In turn, the elastics would not conform to the wearer's body as effectively.

Therefore, there is a need for an elasticized waistband that is safer and/or has a higher assurance of product performance. There is also a need for an article having a waistband that has a high quality garment-like appearance. Further, there is a need for a process for creating an article having a waistband that permits more freedom for manufacturing variability and/or permits the spacing of elastics to be independent of manufacturing constraints and/or process variability. Further still, there is a need for a cost efficient and effective process for manufacturing articles with elasticized waistbands.

SUMMARY OF THE INVENTION

In an embodiment, an absorbent article for wearing about the lower torso of a wearer includes a first waist region having a first waist edge, a second waist region having a second waist edge and a crotch region disposed between the first and second waist regions. The article further includes longitudinal edges and a chassis that includes a topsheet, backsheet and absorbent core disposed between the topsheet and backsheet. A waist gasketing element is joined to the chassis and disposed in one of the first waist region or the second waist region. The waist gasketing element has a top layer and a bottom layer, an inboard lateral edge and an outboard lateral edge, and a first area, A1. The top layer is bonded to the bottom layer in a closure bond region. The closure bond region comprises an aggregate closure bond area, BA, which is at least about 10% of the first area, A1. The waist gasketing element may additionally comprise elastic members.

In a further embodiment, an absorbent article for wearing about the lower torso of a wearer includes a first waist region having a first waist edge, a second waist region having a second waist edge and a crotch region disposed between the first and second waist regions. The article further includes longitudinal edges and a chassis that includes a topsheet, backsheet and absorbent core disposed between the topsheet and backsheet. A first waist gasketing element is joined to the chassis and disposed in the first waist region. The first waist gasketing element has a top layer and a bottom layer. The top and bottom layers are bonded in a first closure bond region. The article further includes a second waist gasketing element joined to the chassis and disposed in the second waist region. The second waist gasketing element has a top layer and a bottom layer, and the top and bottom layers are bonded in a second closure bond region. One or both of the waist gasketing elements may additionally comprise elastic members.

In another embodiment, an absorbent article for wearing about the lower torso of a wearer includes a first waist region having a first waist edge, a second waist region having a second waist edge and a crotch region disposed between the first and second waist regions. The article further includes longitudinal edges and a chassis that includes a topsheet, backsheet and absorbent core disposed between the topsheet and backsheet. A waist gasketing element is joined to the chassis and disposed in the first or the second waist region. The waist gasketing element has a top layer and a bottom layer, an outboard lateral edge and an inboard lateral edge, and includes two or more bonding techniques. The two or more bonding techniques may be internal to the waist gasketing element (i.e., between the top and bottom layer).

Methods for creating articles with waist gasketing elements are also disclosed.

BRIEF DESCRIPTION OF THE DRAWINGS

FIG. 2 is a schematic cross-sectional view of the exemplary rear waist gasketing element in FIG. 1 taken along the longitudinal centerline.

FIG. 3 is a schematic plan view of an exemplary embodiment of a waist gasketing element as detailed herein. The waist gasketing element is shown in a flat, uncontracted state.

FIG. 4 is a schematic plan view of an exemplary embodiment of a waist gasketing element as detailed herein. The waist gasketing element is shown in a flat, uncontracted state.

FIG. 5 is a schematic plan view of an exemplary embodiment of a waist gasketing element as detailed herein. The waist gasketing element is shown in a flat, uncontracted state.

FIG. 11 is a schematic cross-sectional view of an exemplary embodiment of one of the leg gasketing systems of FIG. 1, taken along the lateral centerline. The leg gasketing system is shown in a flat, uncontracted state.

FIG. 12 is a schematic cross-sectional view of an exemplary embodiment of the leg gasketing systems and topsheet of FIG. 1, the cross section taken along the lateral centerline. The leg gasketing systems are shown in a flat, uncontracted state.

DETAILED DESCRIPTION OF THE INVENTION

Definitions

Figure 1:
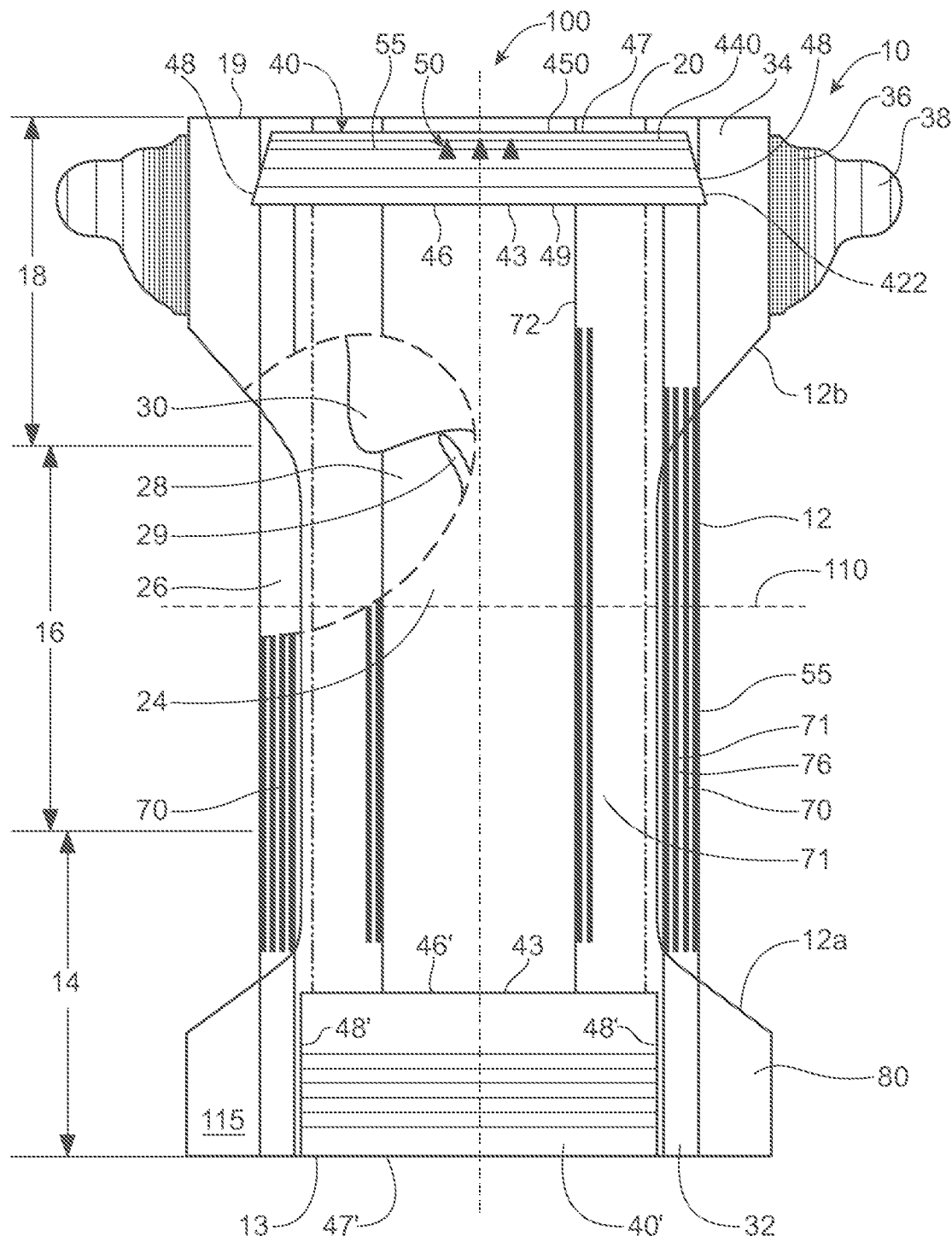
FIG. 1 is a schematic plan view of an exemplary embodiment of an absorbent article as detailed herein. The absorbent article is shown in a flat, uncontracted state.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Bonding technique" refers to the manner in which a bond is formed, including but not limited to bonding material and/or method (e.g., adhesive, ultrasonic, heat etc.), bonding patterns or lack thereof, intermittency or continuity within bonding regions, bond shape, bond size, and bond area or aggregate bond area. Bonding techniques include adhesive bonding, mechanical bonding, pressure bonding, ultrasonic bonding, heat bonding and workable combinations thereof. Suitable bonding techniques may additionally include a pattern of bond sites, continuous or intermittent bonding, a random assortment bond sites, or any workable combination thereof.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is nearer to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal." Longitudinal distances are measured between points disposed along a longitudinal line.

"Lateral" refers to a direction running from a longitudinal edge to an opposing longitudinal edge of the article and generally at a right angle to the longitudinal direction. Directions within 45 degrees of the lateral direction are considered to be "lateral." Lateral distances are measured between points disposed along a lateral line.

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor (i.e., may be "vapor-permeable").

"Elongatable," "extensible," or "stretchable" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery). Elastomeric materials may include elastomeric films (including but not limited to films derived from rubber and/or other polymeric materials), polyurethane films, elastomeric foams, scrims, elastic nonwovens, synthetic fibers such as LYCRA® and other sheet-like structures. An elastic member comprises elastomeric material.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

Absorbent Article

FIG. 1 is a plan view of an exemplary, non-limiting embodiment of an absorbent article 10 of the present invention in a flat, uncontracted state. The body-facing surface 115 of the absorbent article 10 is facing the viewer. The absorbent article 10 includes a longitudinal centerline 100 and a lateral centerline 110.

The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article 10 which, when worn, encircle the waist of the wearer. The waist regions 14 and 18 may include elastic members 55 such that they gather about the waist of the wearer to provide improved fit and containment. The crotch region 16 is the portion of the absorbent article 10 which, when the absorbent article 10 is worn, is generally positioned between the legs of the wearer.

The outer periphery of the chassis 20 is defined by longitudinal edges 12 and waist edges (first waist edge 13 in first waist region 14 and second waist edge 19 in second waist region 18). The longitudinal edges 12 may be subdivided into a front longitudinal edge 12a, which is the portion of the longitudinal edge 12 in the first waist region 14, and a rear longitudinal edge 12b, which is the portion of the longitudinal edge 12 in the second (rear) waist region 18. The chassis 20 may have opposing longitudinal edges 12 that are oriented generally parallel to the longitudinal centerline 100. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 110.

The chassis 20 may comprise a liquid permeable topsheet 24, a backsheet 26, and an absorbent core 28 between the topsheet 24 and the backsheet 26. In embodiments that include one or more opacity strengthening patches 80, the chassis 20 also comprises the opacity strengthening patch(es) 80. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 30 is disposed between the topsheet 26 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet:

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The specific examples are not limiting, as any lotion or skin care composition known in the art may be utilized. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. In one nonlimiting example, two channels are symmetrically disposed about the longitudinal axis.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 62/210,100.

Backsheet:

The backsheet 26 is generally positioned such that it may be at least a portion of the garment-facing surface of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Acquisition-Distribution System (ADS)

The absorbent article may comprise an ADS 30. One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise a distribution layer and/or an acquisition layer disposed between the absorbent core and the topsheet. Suitable ADS are described in WO 2000/59430, WO 95/10996, U.S. Pat. No. 5,700,254, and WO 02/067809, for example.

Ears/Fasteners:

The absorbent article 10 may include front ears 32 and/or back ears 34. The ears 32, 34 may be extensible, inextensible, elastic, or inelastic. The ears 32, 34 may be formed from nonwoven webs, woven webs, knitted fabrics, polymeric and elastomeric films, apertured films, sponges, foams, scrims, and combinations and laminates thereof. In some embodiments, the ear 32, 34 may include elastomers (e.g., elastic strands, LYCRA® fibers), such that the ear is stretchable. In certain embodiments, the ears 32, 34 may be formed of a stretch laminate such as a nonwoven/elastomeric material laminate or a nonwoven/elastomeric material/nonwoven laminate, which also results in the ear being stretchable. Stretch laminates may be formed by any method known in the art. For example, the ears 32, 34 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 20, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the ear 32, 34 are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332).

An ear 32, 34 may be highly extensible wherein the ear 32, 34 is capable of extending up to 150%. It is believed that highly extensible ears 32, 34 allow an absorbent article 10 to expand to comfortably fit a range of wearers who vary in shape and/or weight. Suitable highly extensible ears are described in U.S. Pat. Nos. 4,116,892, 4,834,741, 5,143,679; 5,156,793; 5,167,897; and 5,422,172; and 5,518,801; PCT App. No. WO 2005/110731; and U.S. App. Nos. US 2004/0181200 and US 2004/0193133.

The ears 32, 34 may be integral with the chassis or discrete. A discrete ear is formed as separate element which is joined to the chassis 20.

The absorbent article 10 may also include a fastening system 36. When fastened, the fastening system 36 interconnects the first waist region 16 and the rear waist region 18 resulting in a waist circumference that may encircle the wearer during wear of the absorbent article 10. The fastening system 36 may comprise a fastener 38 such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 36 may also provide a means for holding the article in a disposal configuration as disclosed in U.S. Pat. No. 4,963,140. The fastening system 36 may also include primary and secondary fastening systems, as disclosed in U.S. Pat. No. 4,699,622. The fastening system 36 may be constructed to reduce shifting of overlapped portions or to improve fit as disclosed in U.S. Pat. Nos. 5,242,436; 5,499,978; 5,507,736; and 5,591,152. In some embodiments, the fastening system 36 and/or the fastener 38 is foldable.

The fastening system 36 may be joined to any suitable portion of the article 10 by any suitable means. In some embodiments, the fastening system is joined to the ear 32, 34. In one nonlimiting example, the fastening system 36 and/or the fastener 38 is mechanically bonded to the ear 32, 34 through one or more mechanical bonds.

Waist Gasketing Element

The disposable absorbent article 10 may include at least one waist gasketing element 40 attached to the chassis 20. The waist gasketing element 40 may be disposed on the body-facing side 115 of the chassis or a body-facing side of a layer of the chassis 20; or the waist gasketing element may be disposed on the garment-facing side of the chassis or a garment-facing side of a layer of the chassis. Alternatively, the waist gasketing element 40 may be disposed between the topsheet 24 and the backsheet 26. In an embodiment, the waist gasketing element 40 comprises an elasticized waistband comprising one or more elastic members 55 as shown in FIG. 1. Waist gasketing elements 40 may be joined to the chassis 20 in the first waist region 14 and/or in the second waist region 18. In one nonlimiting example, the waist gasketing element 40 is disposed in the second waist region 18. Waist gasketing elements 40 may be joined to the chassis 20 by a chassis attachment bond 42 as shown in FIG. 2 for example. (FIG. 2 is a schematic cross sectional view of the waist gasketing element disposed in the second waist region of FIG. 1.) The chassis bond 42 may be formed by any suitable bonding technique, including but not limited to adhesive bonding, mechanical bonding, pressure bonding, ultrasonic bonding, heat bonding and combinations thereof. In one nonlimiting example, the chassis bond 42 is an adhesive bond.

In an embodiment, the waist gasketing element 40 comprises a waist gasketing element pocket 43. The pocket 43 may be formed from a portion of the waist gasketing element 40 that is unattached from the chassis 20.

The waist gasketing element 40 comprises a top layer 44 and a bottom layer 45. The top layer and/or the bottom layer may comprise a nonwoven, a film, a laminate of nonwovens and/or films, or combinations thereof. In one embodiment, the waist gasketing element 40 comprises a single, continuous web of material and therefore the top and bottom layers 44, 45 are integral and may be formed by folding the single, continuous web. In other embodiments, the waist gasketing element(s) 40 may be formed from more than one web of material (e.g., multiple webs of material that are joined together to become one web of material, or multiple distinct webs of material that are separate from the disposable absorbent article chassis and form part of the waist gasketing element). In such embodiments, the top layer 44 may be a formed form a different web of material than that of the bottom layer 45. The component materials in the distinct webs may be the same or they may be different. In some embodiments, neither the top layer nor the bottom layer is integral with the chassis (i.e., the waist gasketing element is discrete from the chassis). In alternative embodiments, the top layer 44 may comprise a layer of the chassis 20 such as the topsheet 24. In still further embodiments, the bottom layer 45 may comprise a layer of the chassis 20, including but not limited to the topsheet or the backsheet 26.

Herein, locations (e.g., folded edge, material edge, etc.) on the waist gasketing element 40 are detailed in reference to "a web of material", "a portion of the web of material" or "waist gasketing material." The recitations of "a web of material" or "the web of material" or "waist gasketing material" refer to waist gasketing element embodiments that may be formed from a single, continuous web of material, multiple webs of material that are joined together to become one web of material, a single material that is folded to form multiple layers of the same material, a single material that is slit apart and rejoined together, or multiple distinct webs of material that may be separate from the disposable absorbent article chassis and form part of the waist gasketing element 40. All such embodiments are contemplated.

The waist gasketing element 40 includes an inboard lateral edge 46, an outboard lateral edge 47, and two longitudinal edges 48 as shown for example in FIGS. 1 and 2. The outboard lateral edge 47 may be coterminous with a waist edge 13, 19. Alternatively, the outboard lateral edge 47 may be disposed longitudinally inward of the waist edge 13, 19. The periphery of the waist gasketing element (e.g., the lateral and longitudinal edges) defines a waist gasketing element area, A1 (i.e., the mathematical, two-dimensional area of the waist gasketing element).

In further embodiments, the web of material forming the waist gasketing element 40 is folded longitudinally outward (away from the lateral centerline 110 of the absorbent article 10) to form the inboard lateral edge 46. In such embodiments, the inboard lateral edge 46 comprises a folded edge 49 and the outboard lateral edge 47 comprises a first material edge 440, which may be the material edge of the top layer 44 and a second material edge 450 which may comprise the material edge of the bottom layer 45. Although an embodiment depicting a waist gasketing element 40 with one folded edge 49 and two material edges 440, 450 is shown in FIG. 2, alternate constructions of useful waist gasketing elements are contemplated. For example, an alternate waist gasketing element 40 may include two distinct webs of material and therefore have four material edges (two on the inboard lateral edge 46, and two on the outboard lateral edge 47 or said differently, two opposed edges on the top layer 44 and two opposed edges on the bottom layer 45). As another nonlimiting example, an alternate waist gasketing element 40 may have a continuous web material that is formed into having two folded edges (one on the inboard lateral edge 46, and one on the outboard lateral edge 47) and two longitudinal material edges.

In a further embodiment, the waist gasketing element 40 may be used in conjunction with a leg gasketing system 70 as shown in FIG. 1. In such embodiment, the waist gasketing element 40 is attached to: 1) the chassis 20 and 2) the leg gasketing system 70, such that at least a portion of the outboard lateral edge 47 of the waist gasketing element 40 is attached to the chassis 20 and at least a portion of the outboard lateral edge 47 of the waist gasketing element 40 is attached to the web of material of the leg gasketing system 70. The inboard lateral edge 46 of the waist gasketing element 40 may be unattached to the chassis 20 of the disposable absorbent article 10. In embodiments that include a waist gasketing element 40 that has a waist gasketing element folded edge 49, a waist gasketing element first material edge 440, and a waist gasketing element second material edge 450, at least a portion of the web of material between the waist gasketing element folded edge 49 and waist gasketing element second material edge 450 is attached to the topsheet 24 and/or backsheet 26 of the chassis 20.

The attachment of the waist gasketing element 40 to the chassis 20 is made through utilization of one or more chassis attachment bonds 42. Exemplary chassis attachment bonds are illustrated in FIGS. 1-3. (FIG. 3 is a plan view of exemplary embodiments of the surface 40A of exemplary waist gasketing elements 40 that would be attached to the chassis 20.) As can be seen in FIG. 3, the chassis attachment bonds 42 may comprise outboard lateral edge bonds 420. An outboard lateral edge bond 420 attaches at least a portion of the waist gasketing element's web of material to the topsheet 24 and/or backsheet 26. In one embodiment, the outboard lateral edge bond 420 is at least partially coterminous with a waist edge; in other embodiments, the outboard edge bond 420 is placed longitudinally inboard from a waist edge by at least 2 mm, or at least 10 mm, or at least 20 mm, or at least 50 mm; or any range or distance within the range of about 2 mm to about 50 mm. The outboard lateral edge bond 420 may take the form of an adhesive bond, heat bond, pressure bond, mechanical bond, or any other bonding technique known in the art. In some embodiments, an outboard lateral edge bond 420 takes the form of an adhesive bond. In some further embodiments, the chassis attachment bonds 42 further comprise inboard lateral edge bonds 421 disposed on the inboard lateral edge 46 or any longitudinal distance within the range of about 0 mm to about 4 mm from the inboard lateral edge. The lateral edge bond(s) 420, 421 may comprise continuous and/or intermittent edge bonds.

In some embodiments, chassis attachment bonds 42 may comprise longitudinal edge bonds 422. In embodiments that include a waist gasketing element 40 that has a folded edge 49, a waist gasketing element first material edge 440, and a waist gasketing element second material edge 450, at least a portion of the web of material between the waist gasketing element folded edge 49 and waist gasketing element second material edge 450 may be attached to the web of material forming the leg gasketing system 70. The attachment of the waist gasketing element 40 to the web of material forming the leg gasketing system 70 may be made through utilization of one or more longitudinal edge bond(s) 422. As seen in the embodiment of FIG. 1, the longitudinal edge bonds 422 attach at least a portion of the waist gasketing element's web of material between the waist gasketing element folded edge 49 and the waist gasketing element second material edge 450 to the web of material forming the leg gasketing system 70. The longitudinal edge bonds 422 can be located adjacent to the longitudinal edges 48 of the waist gasketing element 40 (or may be coterminous therewith). In another embodiment, the longitudinal edge bonds 422 are located adjacent to an inner cuff folded edge 72 of the leg gasketing system 70 (or may be coterminous therewith). The waist gasketing element 40 may be attached to the leg gasketing system 70 over substantially the entire area that the leg gasketing system 70 overlaps with the waist gasketing element 40. In some embodiments, the waist gasketing element 40 is attached to the leg gasketing system 70 over more than about 50%, more than about 60%, more than about 70%, more than about 80%, more than about 90%, or more than about 95%, of the entire area that the leg gasketing system 70 overlaps with the waist gasketing element 40. The longitudinal edge bonds 422 may take the form of adhesive bonds, heat bonds, pressure bonds, mechanical bonds, or any other bonding technique known in the art. In one nonlimiting example, a longitudinal edge bond 422 takes the form of an adhesive bond. The longitudinal edge bond(s) 422 may comprise continuous and/or intermittent edge bonds.

In one nonlimiting example, the combination of the longitudinal edge bonds 422, the lateral outward edge bond 420 and unattached portion of the inboard lateral edge 46 of the waist gasketing element 40 (i.e., unattached from the chassis 20) forms a pocket 43. When the wearer moves, a portion of the bodily exudates will migrate into the waist gasketing element pocket 43 for containment and be held/trapped between two layers of nonwoven before it can leak out in an area between the wearer's back and the back waist region 18 of the absorbent article 10. In addition, the waist gasketing element pocket 43 provides additional void volume within the waist region to receive the fecal material which helps in isolating the fecal material from wearer's skin.

As can be seen in FIGS. 2, 4 and 5, the waist gasketing element 40 may comprise a closure bond region 50. In the closure bond region 50, the top layer 44 of the waist gasketing element 40 is joined to the bottom layer 45 by one or more closure bonds 51. Each closure bond 51 attaches the top layer 44 to the bottom layer 45. A closure bond 51 may further attach the waist gasketing element to one or more layers of the chassis, and thereby also serve as the chassis attachment bond 42. Additionally or alternatively, a closure bond 51 may further attach the waist gasketing element to another component, such as the leg gasketing system 70. In some embodiments, a closure bond 51 may attach a component (e.g., leg gasketing system, opacity patch) to the chassis in the waist region. In nonlimiting examples, a closure bond 51 may extend through the waist gasketing element and chassis (i.e., the bond may attach all layers of the waist gasketing element and the chassis). In some nonlimiting examples, the closure bond 50, alone or in combination in with additional bond(s), may form a pocket 43. The pocket 43 may facilitate retention of excrement and prevent leakage.

In one nonlimiting example, the closure bond region 50 comprises a closure bond 51 in the form of a continuous bar 52 as shown in FIG. 4. (FIG. 4 is a plan view of a waist gasketing element showing the closure bond region.) The continuous bar may be straight, curvilinear or any suitable shape. In some embodiments, a continuous bar is in the form of a continuous non-rectangular shape. Alternatively, the closure bond region 50 comprises multiple, discrete closure bonds 51, as shown for example in FIG. 5. (FIG. 5 is a plan view of a waist gasketing element showing an alternative embodiment of the closure bond region.) Where multiple closure bonds 51 are utilized, the bonds 51 may be in the form of multiple stripes, dots, or any other suitable shape or suitable combination of shapes. The closure bonds 51 may be disposed intermittently such that at least two bonds are separated by a separation span 54. The separation span 54 may comprise a maximum lateral width, X, of about 15 mm or less, or about 10 mm or less, or about 5 mm or less, or about 4 mm or less. Alternatively or additionally, the closure bond region 50 comprises closure bonds 51 in the form of a pattern 53.

The closure bond(s) 51 may be formed by any suitable bonding technique or suitable combination of different bonding techniques. In one nonlimiting example, one or more closure bonds 51 comprise adhesive bonds. Suitable adhesive materials are Bostik H2401 available from Bostik Inc. of Wauwatosa, Wis. and P Adhesive HB Fuller D3166 BC8 F ZP available from H. B. Fuller of St. Paul, Minn. An adhesive bond may be applied by slot coating. Additionally, or alternatively, the adhesive may have a basis weight of about 3 gsm or more, or from about 3 gsm to about 10 gsm, or about 10 gsm or less, reciting for said range every 1 gsm increment therein. In this way, the region 50 can be provided with sufficient bonding while maintaining softness and minimizing adhesive costs.

In certain embodiments, a closure bond 51 may be formed by a mechanical bond. In nonlimiting examples, a mechanical bond may be used in combination with adhesive bonds in the closure bond region. In such examples, the amount of adhesive can be reduced, helping to minimize costs, while maintaining sufficient bond strength. In nonlimiting examples, mechanical bonds may be applied along one or more edges 46, 47, 48 of the waist gasketing element and/or one or more edges of the closure bond region. In further nonlimiting examples, mechanical closure bonds 51 are applied in overlapping relationship with one or more elastic members 55.

In some embodiments, the closure bond region 50 is at least partially disposed on the outboard lateral edge 47, as shown in FIG. 4. In other embodiments, the closure bond region 50 has an outboard edge that is a maximum longitudinal distance Y of 4 mm or less from the outboard lateral edge 47, as can be seen in FIG. 5. The skilled person will recognize that the distance, Y, from the outboard lateral edge may change depending on the size and area of the waist gasketing element, the size and area of the article, the size and area of the closure bond region, the strain of one or more elastics in the closure bond region, the bond strength of closure bonds and/or the bond strength of elastic bonds (discussed below) and the like.

Each closure bond 51 comprises an individual bond area (i.e., the two dimensional, mathematical area of the bond). The closure bond region 50 comprises an aggregate closure bond area, BA, which is the sum of the individual bond areas of each closure bond 51. In some embodiments, the closure bond area is less than the waist gasketing element area, A1. The closure bond area, BA, may be from about 5% to about 100%, or from about 8% to about 90%, or from about 10% to about 60%, or at least about 10%, or at least about 13%, or at least about 15%, or at least about 17%, or at least about 20%, or at least about 25%, or less than about 90%, or less than about 75%, or less than about 60% of the waist gasketing element area, A1, reciting for each range every 5% increment therein.

The closure bond region 50 comprises a maximum lateral width, $W_{CB}$, and a maximum longitudinal length, $L_{CB}$. In certain embodiments, the maximum longitudinal dimension, $L_{CB}$, is less the maximum lateral dimension, $W_{CB}$. In further embodiments, the maximum lateral width, $W_{CB}$, may extend across the entire lateral dimension of the waist gasketing element as shown in FIG. 5. Alternatively, the maximum lateral dimension, $W_{CB}$, may be less than the maximum lateral width, W, of the waist gasketing element as shown in FIG. 4. Similarly, the closure bond region 50 the maximum longitudinal dimension, $L_{CB}$, may be less than or equal to the maximum longitudinal dimension, L, of the waist gasketing element.

In embodiments where an article comprises two waist gasketing elements (e.g., a front and a rear waist gasketing element), the size relationship between one waist gasketing element and its closure bond region may differ from the size relationship between the second waist gasketing element and its closure bond region.

Without wishing to be bound by theory, the optimal closure bond region dimensions will vary based on number of considerations, including but not limited to the component materials of the top and bottom layers, process conditions including but not limited to line speed and converting operations such as cutting near or on the waist gasketing elements, the bonding technique including but not limited to bonding material and add-on levels, the dimensions of the waist gasketing element and/or chassis, the layer of the chassis to which the waist gasketing element is attached, and materials (such as elastic members) which are included in the waist gasketing element.

The waist gasketing element 40 may further comprise one or more laterally extending elastic members 55. In some embodiments, the elastic members may be positioned between i) the portion of the web of material between a waist gasketing element folded edge 49 and the waist gasketing element first material edge 440, and ii) the portion of the web material between the waist gasketing element folded edge 49 and the waist gasketing element second material edge 450.

The elastic members 55 may be elastomeric fibers, such as LYCRA® fibers available from INVISTA of Wichita, Kans., in various decitex levels. The skilled person may select the appropriate decitex based on the desired contraction and other principles discussed herein. Other suitable elastics can be made from natural rubber, such as elastic tape sold under the trademark Fulflex 9411 by Fulflex Company of Middletown, R.I. The elastic members 55 may also comprise any heat shrinkable elastic material as is well known in the art. In addition, elastic members 55 may take a multitude of configurations. For example, the width may be varied; a single strand or several parallel or non-parallel strands of elastic material may be used; or a variety of shapes may be used including rectilinear and curvilinear; or a variety of cross sectional shapes can be used (circular, rectangular, square, etc.).

The waist gasketing element 40 may comprise at least two waist elastic members 55, at least three waist elastic members 55, at least four elastic members 55, at least five elastic members 55, at least six waist elastic members 55, at least seven waist elastic members 55, at least eight waist elastic members 55, at least nine waist elastic members 55, at least ten waist elastic members 55, at least eleven waist elastic members 55, or at least twelve waist elastic members 55.

In one embodiment, adjacent elastic members 55 are spaced a longitudinal distance of at least 3.5 mm apart from one edge of the member to the other edge of the member, optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The spacing between elastic members may be the same or different across the longitudinal length of the waist gasketing element. For example, the spacing between adjacent elastic members could uniformly be 7 mm or there could be variable spacing (i.e., two adjacent elastic members are separated by 3 mm, another two are separated by 6.5 mm, etc.).

One or more elastic members 55 may be joined to the top layer 44 and/or the bottom layer 45 of the waist gasketing element 40. The elastic members 55 may be joined to waist gasketing element 40 by one or more elastic bonds 56, illustrated in FIGS. 4-6 for example. An elastic member 55 may be joined to the gasketing element 40 by one continuous bond 57 (see FIG. 4) or intermittently, such that bonds 56 are separated by separation spans 58 (also depicted in FIG. 4).

Elastic bonds 56 may be formed by any suitable bonding technique. In some embodiments, intermittent elastic bonds are formed through patterned slot coating techniques as taught in U.S. Pat. Pub. Nos. 2014/0148323, 2014/0148773, 2014/0148774 and 2014/0144579. The bonding technique(s) utilized in forming an elastic bond 56 may be the same or may be different from the bonding technique(s) utilized in forming a closure bond 51. In some embodiments, more than one bonding technique is utilized in forming bonds 51, 56 in one waist gasketing element 40. In one nonlimiting example, one or more elastic bonds comprise adhesive bonds. The type of adhesive used in forming an elastic bond may be the same as or may differ from type of adhesive material used in forming a closure bond. In some nonlimiting examples, the elastic bonds are formed by strand coating, spiral coating or combinations thereof.

Each elastic bond 56 may comprise an elastic bond area (i.e., the two dimensional, mathematical area of the bond). The waist gasketing element 40 may comprise an aggregate elastic bond area, EA, which is the sum of the individual elastic bond areas within the waist gasketing element. The aggregate elastic bond area, EA, may be less than the aggregate closure bond area, BA. In some embodiments, the aggregate elastic bond area is about 30% or less, or about 20% or less, or about 10% to about 30% of the aggregate closure bond area, reciting for said range every 5% interval therein.

Figure 6:
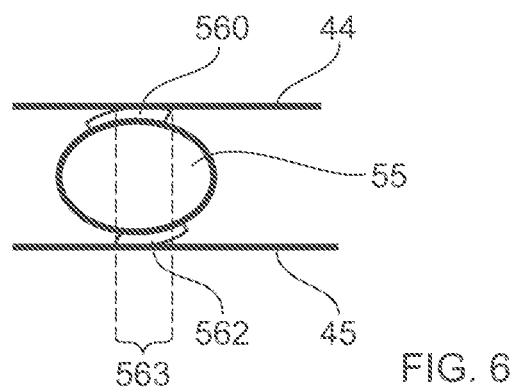
FIG. 6 is a schematic partial, side elevation view of an exemplary embodiment of a waist gasketing element as detailed herein.

In some embodiments, an elastic member 55 will be attached to the top layer 44 comprising a top bond 560. In further embodiments, an elastic member will be attached to the bottom layer 45 comprising a bottom bond 562. An elastic member may be attached to both the top and bottom layers, comprising both top and bottom bonds as shown in FIG. 6. In such embodiments, the top and bottom bonds may be formed by the same bonding techniques or by different bonding techniques. Further, in such embodiments, the elastic bond area is the sum of the areas of the top and bottom bonds, provided however that any overlapping coverage area 563 is counted only once.

In certain embodiments, the waist gasketing element 40 comprises adjacent elastic members 55 that are joined to the waist gasketing element 40 by a different bonding technique (e.g., different bonding materials, patterns, etc.). In one such embodiment shown in FIG. 4, a first elastic member 550 may be adjacent to the second elastic member 555. The first elastic member 550 may be intermittently joined to the waist gasketing element 40 by bonds 56 that are separated by separation spans 58. The second elastic member 555 can be continuously joined to the waist gasketing element 40 by one continuous elastic bond 57. Examples of ways to differently join adjacent elastics are disclosed in U.S. Patent App. No. 62/186,727.

Further, waist elastic members 55 may be differentially strained. Strain may be provided to an elastic member 55 by stretching said elastic member 55 prior to joining said elastic member 55 to the waist gasketing element 40. In general, strain is the difference between the stretched length ($l_1$) of an elastic member 55 and the relaxed length ($l_2$) of the same elastic member 55 (i.e., strain is $l_1-l_2$). One of skill in the art will recognize that the magnitude of strain differences in comparative elastic members 55 during manufacturing may be different than the magnitude of the strain differences of those same comparative elastic members 55 in the final product; however, the relationship between the elastic members' strain (i.e., one is greater than the other) may remain apparent in the final article 10. In one embodiment, adjacent elastic members 55 comprise strain levels that differ by at least about 50%, or from about 75% to about 200%, or about 100% to about 150%, reciting for each range every 10% increment therein, when said elastic members are joined to the waist gasketing element 40.

Figure 7:
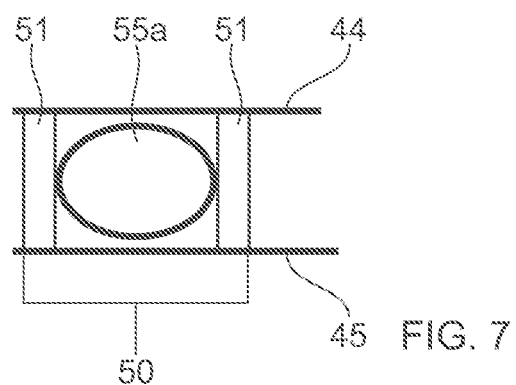
FIG. 7 is a schematic partial, side elevation view of an exemplary embodiment of a waist gasketing element as detailed herein.

As can be seen in FIGS. 4-5 and 7 for example, a closure bond region 50 may overlay one or more elastic members 55, such that the closure bond region 50 encases said elastic members while bonding the top and bottom layers 44, 45 surrounding the elastic members. FIG. 4 illustrates an embodiment where the encased elastic members 55a are joined to the top and/or bottom layers of the waist gasketing element by elastic bonds 56. FIG. 5 depicts an embodiment where the encased elastic members 55a are free from elastic bonds 56. Stated differently, elastic bonds 56 may be disposed in areas where closure bonds 51 are not present and vice versa.

Figure 8:
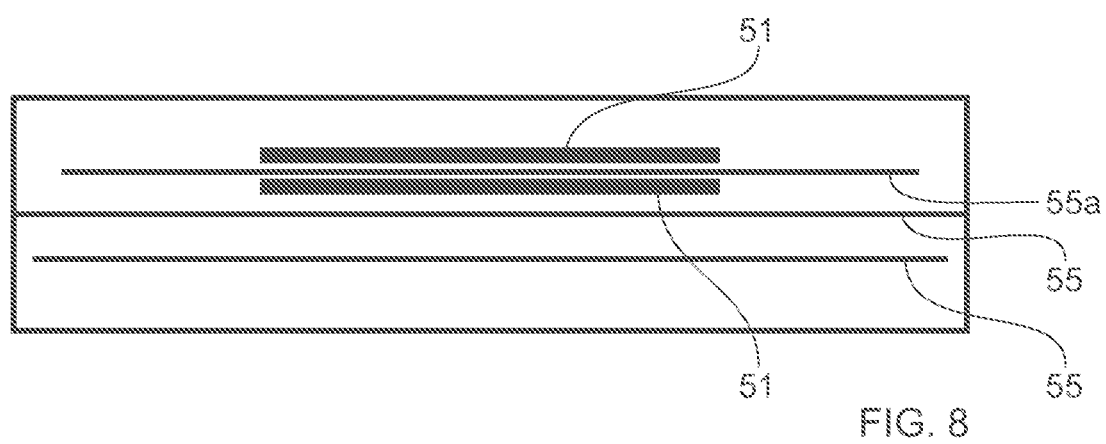
FIG. 8 is a schematic plan view of an exemplary embodiment of a waist gasketing element as detailed herein. The waist gasketing element is shown in a flat, uncontracted state.

Further to the above, FIGS. 7 and 8 depict embodiments where closure bonds are close to but not overlapping an elastic member 55a that is encased in the closure bond region. Such positioning minimizes the risk of delamination of the waist gasketing element layers around the elastic member while also minimizing the amount of bonding material required and minimizing the dampening effect that bonding has on elasticity.

Figure 9:
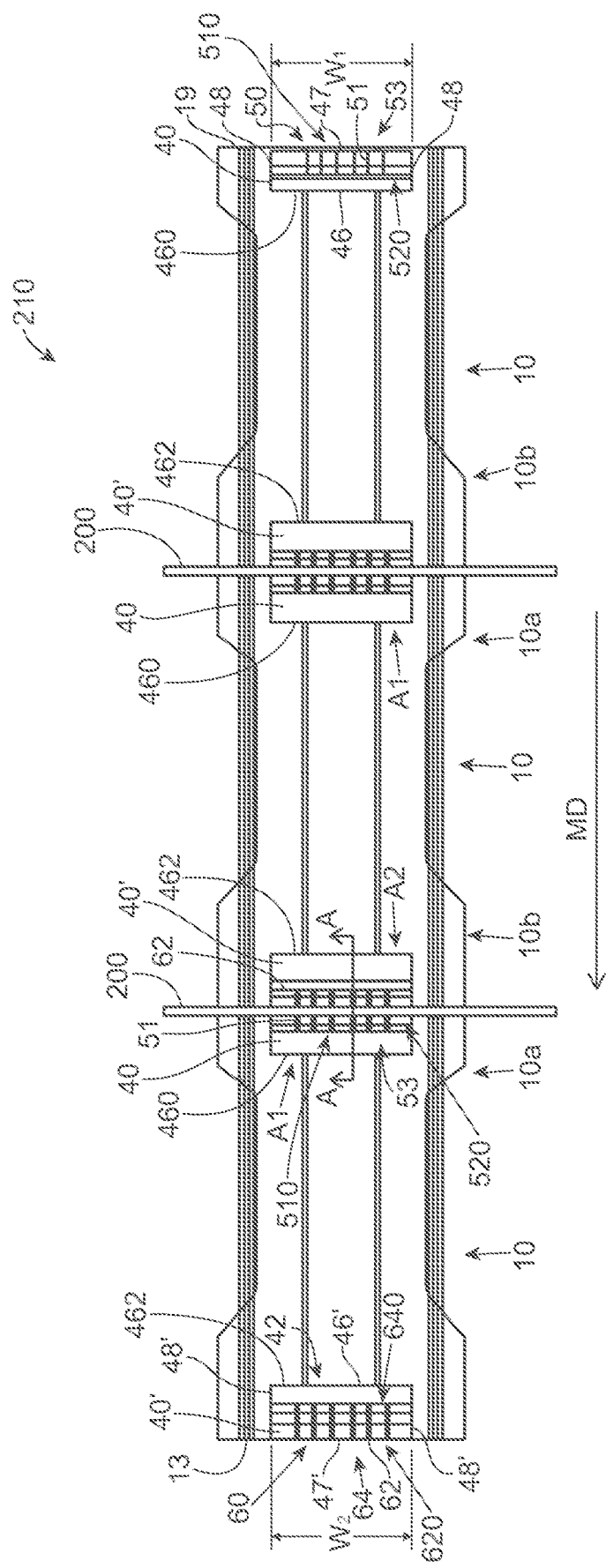
FIG. 9 is a schematic plan view of an exemplary embodiment of a web of multiple absorbent articles.
Figure 10A:
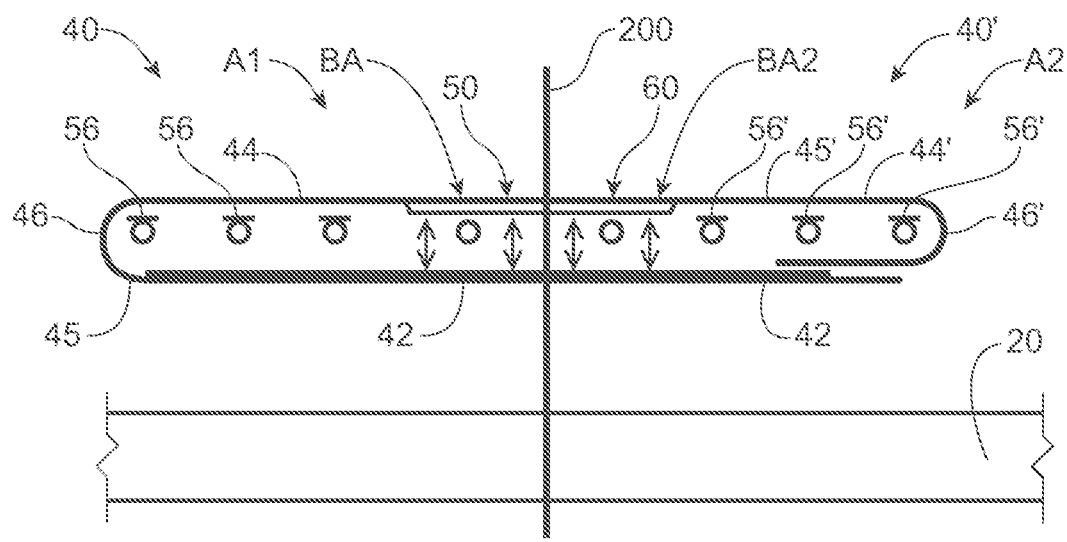
FIGS. 10A and 10B are schematic cross-sectional views of the exemplary web of FIG. 9 taken along line A-A.
Figure 10B:
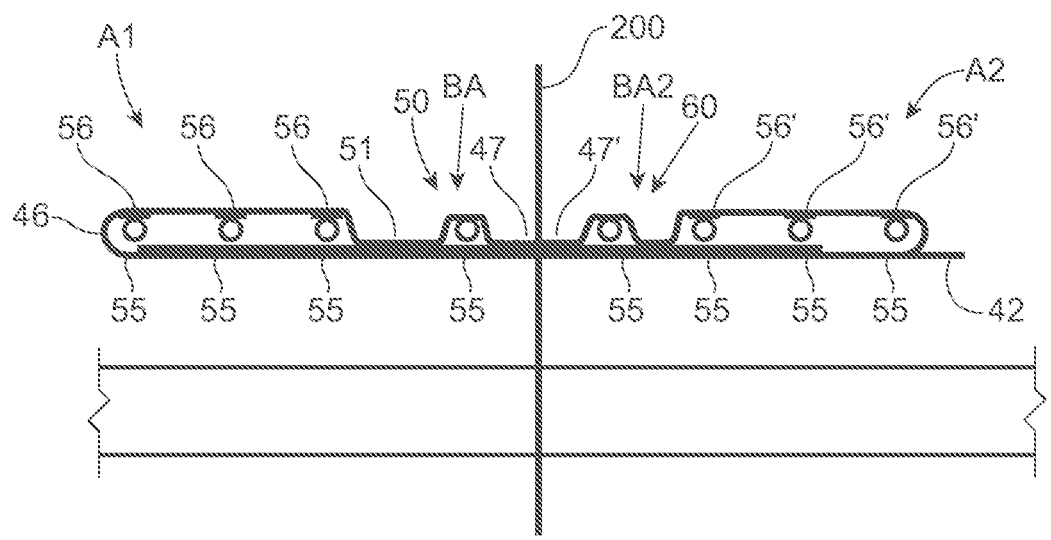

Turning to FIGS. 9-10B, an article 10 may further comprise a second waist gasketing element 40'. (FIG. 9 is a schematic representation of a web of articles and a separating apparatus. FIG. 10A is a schematic cross-sectional representation of a waist gasketing element of FIG. 9 taken along line A-A before bonds are engaged. FIG. 10B is a schematic cross-sectional representation of the waist gasketing element after bonding within the waist gasketing element.) The second waist gasketing element 40' may comprise any of the features described herein with respect to the waist gasketing element 40 (also referred to going forward as the first waist gasketing element 40). By way of nonlimiting example, the second waist gasketing element 40' comprises a top layer 44', a bottom layer 45', an inboard lateral edge 46', outboard lateral edge 47', and longitudinal side edges 48'. Similar to the first waist gasketing element, the top and bottom layers of the second waist gasketing element may be formed from a single web of material or multiple webs of materials. In some embodiments, the top layer 44' and/or the bottom layer 45' may be formed by portions of the chassis 20.

The second waist gasketing element further comprises a second area, A2. The second area may be the same as or may be different than the area, A1, of the first waist gasketing element 40. In an embodiment, the outboard lateral edge 47 of the first waist gasketing element 40 comprises a first width, W1, and the outboard lateral edge 47' of second waist gasketing element comprises a second width, W2. In one nonlimiting example, the first and second widths are the same. Like the first waist gasketing element, the outboard lateral edge 47' of the second waist gasketing element may be coterminous with a waist edge 13, 19 or may be set apart by a longitudinal distance, Y, from the waist edge.

The second waist gasketing element 40' may comprise a second closure bond region 60, wherein the top layer 44' is joined to the bottom layer 45' by one or more second closure bonds 62. The second closure bonds 62 may be formed by any suitable bonding technique or combination of different bonding techniques. In one nonlimiting example, one or more closure bonds 62 comprise adhesive bonds. The second closure bond region 60 may comprise a closure bond 62 in the form of a continuous bar or may comprise multiple closure bonds 62. In a further nonlimiting example shown in FIG. 9, closure bonds 62 may be disposed intermittently such that at least two bonds are separated by a separation span having any of the features of separation spans described with respect to the closure bond region 50 of the first waist gasketing element. In some embodiments, the second closure bonds 62 are disposed in a pattern 64, which may be the same as or may differ from a bonding pattern 53 in the first waist gasketing element. In a further nonlimiting example, the closure bonds 51, 62 in the first and second closure bond regions 50, 60 are formed by different bonding techniques, including but not limited to different bond types, patterns, bonding materials etc.

In an embodiment shown in FIGS. 10A-10B, each second closure bond 62 comprises an individual bond area. The second closure bond region 60 comprises a second aggregate bond area, BA2. The second aggregate bond area, BA2, may be from about 5% to about 100%, or from about 8% to about 90%, or from about 10% to about 60%, or at least about 10%, or at least about 13%, or at least about 15%, or at least about 17%, or at least about 20%, or at least about 25%, or less than about 90%, or less than about 75%, or less than about 60% of the second area, A2, reciting for each range every 5% increment therein. The ratio of the first closure bond area to the area of the first waist gasketing element (BA:A1) may be the same as or may differ from the ratio of the second closure bond area to the area of the second waist gasketing element (BA2:A2). The first aggregate closure bond area, BA, may be the same as or may differ from the second aggregate closure bond area, BA2. While FIGS. 10A and 10B shown the two closure bond regions and two waist bands interconnected, it should be recognized that they can be separated (using the separating apparatus 200) and each be connected to a separate article 10. Thus, FIGS. 10A and 10B illustrate a first waist gasketing element for a first article and a second waist gasketing element to be disposed on a second article. However, it should be understood that the principles stated herein could apply to two waist gasketing elements on a single article.

One or more closure bonds 51 in the first closure bond region may be formed by the same bonding technique as one or more second closure bonds 62. In some embodiments, closure bonds 51 in the first closure bond region are formed by different bonding techniques than second closure bonds 62.

Similar to the first waist gasketing element, the second waist gasketing element may comprise one or more laterally-extending elastic members 55, having any of features described above with respect to elastic members. The elastic members 55 may be joined to the top and/or bottom layers 44', 45' by one or more elastic bonds 56', having any of the above-described features of elastic bonds 56. In certain embodiments, one or more elastic bonds 56' are formed by different bonding techniques than used to form one or more closure bonds 62. In further embodiments, elastic members 55 in the first waist region 14 may be attached by different bonding techniques than elastic members 55 in the second waist region 18. In an alternative embodiment, the elastic bonds in the first waist region 14 may comprise one or more of the same bonding techniques as the elastic bonds in the second waist region 18. Elastic members 55 in the first waist gasketing element may be spaced apart in the same manner as or in a different manner than elastic members 55 in the second waist gasketing element.

In some embodiments, any waist elastic members 55 in the first waist region 14 and/or any waist elastic members 55 in the second waist region 18 may be differentially strained. Further, strain levels in the first waist region 14 may be the same as or different than strain levels in the second waist region 18. In still another embodiment, any adjacent elastic members 55 in the first waist region 14 and/or any adjacent elastic members 55 in the second waist region 18 may be joined to the waist gasketing element 40 by different bonding techniques (e.g., one continuously bonded and the other intermittently bonded, different bonding materials, different bonding patterns, etc.).

Waist gasketing elements of the present invention may comprise bonds that are formed by different bonding techniques. In some embodiments, the different bonding techniques result in bonds that differ by bond type (i.e., adhesive bond, ultrasonic bond, heat bond, mechanical bond etc.), bonding material (e.g. different types of adhesives), bond area, bond strength, bond shape, and/or bond size. The two or more bonding techniques may be applied internally in the waist gasketing element (i.e., the resulting bonds are at least partially disposed between the top and bottom layers).

In further embodiments, two or more bonding techniques may overlap within the waist gasketing element. For instance, an elastic bonding technique may overlap with a closure bonding technique. In one nonlimiting example shown for example in FIG. 9, a waist gasketing element may comprise a closure bonding technique 510, which includes one or more bonding techniques that form the closure bonds 51. The same waist gasketing element may further comprise an elastic bonding technique 520 which includes one or bonding techniques used to form elastic bonds 56. The closure bonding technique may be the same as or may differ from the elastic bonding technique 520. Further to the above, an article 10 may include a second waist gasketing element having a second closure bonding technique 620 and/or a second elastic bonding technique 640. The second closure bonding technique 620 may be the same as or may differ from the closure bonding technique 510 and/or the elastic bonding technique 520 in the first waist gasketing element. Likewise, the second elastic bonding technique 640 may be the same as or may differ from the closure bonding technique 510 and/or the elastic bonding technique 520 in the first waist gasketing element. Further still, the second closure bonding technique and the second elastic bonding technique may be the same or may differ.

In some embodiments, bonds described herein may include colors or pigments. The colors and/or pigments may be visible through the topsheet and/or visible through the backsheet. Patterns 53, 64 and/or intermittent bonding may be formed through patterned slot coating techniques as taught in U.S. Pat. Pub. Nos. 2014/0148323, 2014/0148773, 2014/0148774 and 2014/0144579 in some embodiments.

In an embodiment, the waist gasketing element 40 may comprise N-fiber.

A strip of articles 210 comprising waist gasketing elements 40 may be formed from a web of chassis material 20 and multiple waist gasketing elements as shown in FIG. 9. In some embodiments, the strip of articles 210 is formed by joining a web of chassis material to a plurality of waist gasketing elements (each having a top layer and a bottom layer). In other embodiments, a web of chassis material may comprise a plurality of first layers of a waist gasketing element. The first layer may comprise the top layer 44 or the bottom layer 45 as described above. Second layers (i.e., the other of the top or bottom layer) may be joined to the first layers of the waist gasketing elements to form the strip of articles 210.

Each waist gasketing element in the strip 210 may comprise a first transverse edge 460 and a second transverse edge 462.

The top and bottom layers (or said differently, the first and second layers) of each waist gasketing element may be joined in closure bond regions as discussed above by any suitable bonding technique(s). In some embodiments, more than one bonding technique is utilized. In embodiments where a waist gasketing element is formed by a single web of material, said web of material may be folded to form the top and bottom layers. The top and bottom layers may be joined by a closure bond before or after attachment of the waist gasketing element to the web.

The waist gasketing elements may be disposed apart from one another by a longitudinal distance in the machine direction. A separating apparatus 200 (such as a knife) may be used to separate the strip 210 into individual articles 10. The separating apparatus 200 may cut the strip 210 laterally between the transverse edges 460, 462 of the waist gasketing elements. The separating apparatus 200 may be programmed or otherwise directed to cut at target zones on the strip of articles. However, given manufacturing viabilities, the separating apparatus 200 may not be able to consistently hit the targets. The closure bond region may cover a longitudinal distance and/or lateral distance that encompasses and extends beyond the target zone. In this way, elastic members are less likely to be exposed at the time of separating the articles, even if the separating apparatus 200 does not hit the same target on each article as shown in FIG. 9.

Each cut results in a leading article 10a and a trailing article 10b. The cut forms the back waist edge 19 of the leading article 10a and the front waist edge 13 of the trailing article 10b. The cut may form the outboard lateral edge of a waist gasketing element disposed in the second waist region of the leading article and/or form the outboard lateral edge of a waist gasketing element disposed in the first waist region of the trailing article.

Leg Gasketing System

The absorbent article 10 may comprise a leg gasketing system 70 attached to the chassis 20. The leg gasketing system 70 comprises one or more cuffs 71. The leg gasketing system 70 may be constructed as, and comprise one or more features, disclosed in commonly assigned U.S. App. Nos. 62/134,622; 62/186,727.

FIGS. 11 and 12 depict schematic cross sectional views of the exemplary leg gasketing systems of FIG. 1 in a flat, uncontracted state, the views taken through the lateral centerline 110 (FIG. 11 is a schematic cross section of the left leg gasketing system, and FIG. 12 is a schematic cross section of both leg gasketing systems in relation to the topsheet).

In an embodiment, the leg gasketing system 70 comprises an inner cuff 72 having an inner cuff edge 73. The inner cuff edge 73 may comprise an inner cuff material edge 74. Alternatively, the inner cuff material edge 74 may be folded such that the cuff edge 73 comprises a folded inner cuff edge 75. The leg gasketing system 70 may further comprise an outer cuff 76 that comprises an outer cuff edge 77. The outer cuff edge 77 may comprise the outer cuff material edge 78. Alternatively, the outer cuff material edge 78 may be folded such that the outer cuff edge 77 comprises a folded outer cuff edge 79.

In one embodiment, each leg gasketing system 70 comprises a single, continuous web of material. In other embodiments, the leg gasketing system 70 may be formed from more than one web of material (e.g., multiple webs of material that are joined together to become one web of material, or multiple distinct webs of material that are separate from the disposable absorbent article chassis and form part of the leg gasketing system). Herein, locations (e.g., folded edge, material edge, etc.) on the leg gasketing system 70 are detailed in reference to "a web of material" or "a portion of the web of material." The recitations of "a web of material" or "the web of material" refer to leg gasketing system embodiments that may be formed from a single, continuous web of material, multiple webs of material that are joined together to become one web of material, or multiple distinct webs of material that are separate from the disposable absorbent article chassis and form part of the leg gasketing system. All such embodiments are contemplated.

In some embodiments, the web of material is folded laterally inward (toward the longitudinal centerline 100 of the absorbent article 10) to form the outer cuff folded edge 79 and folded laterally outward (away from the longitudinal centerline 100 of the absorbent article 10) to form the inner cuff folded edge 75.

The cuffs 71 may be attached to the chassis 20 and/or each other 72, 76 by any suitable means. In an embodiment, the outer cuff 76 is attached to the chassis 20 through one or more cuff attachment bonds 82 as illustrated in FIG. 12. Further, a cuff attachment bond 82 may attach at least portion of web material in the outer cuff 76 to the opacity strengthening patch 80 in at least a portion of the first waist region 14 and at least a portion of the second waist region 18 (not shown).

In an embodiment, the inner cuff edge 73 comprises a folded edge 75 and the outer cuff edge 77 comprises a folded outer cuff edge 79. In such embodiment, at least a portion of the web material between the inner cuff folded edge 75 and the outer cuff folded edge 79 can be attached to at least a portion of the web of material between the outer cuff folded edge 79 and the outer cuff material edge 78 in at least the crotch region 16 and the first waist region 14. The attachment of the web of material between the inner cuff folded edge 75 and the outer cuff folded edge 79 to the web of material between the outer cuff folded edge 79 and the outer cuff material edge 78 in at least the crotch region 16 and the first waist region 14 is made through utilization of one or more cuff separation bonds 84. The leg gasketing system 70 may further comprise a pocket 85 arising from the web of material between the inner cuff folded edge 75 and the outer cuff folded edge 79 being unattached to the web of material between the outer cuff folded edge 79 and the outer cuff material edge 78 in one of the waist regions 14, 18 as shown in FIG. 12. The pocket 85 may provide additional void volume within the leg gasketing system 70 to receive exudates to help isolate fecal material from the wearer's skin as well as contain exudates between the layers of the leg gasketing system 70 to prevent leakage. The pocket 85 may comprise an opening created by a break in the cuff separation bond 84 or a series of breaks in the cuff separation bond 84. The pocket and opening can occur in the first waist region 14, the second waist region 18 or the crotch region 16 as needed for the specific type of exudates and particular situation where leakage prevention is desired. Attachment of the outer cuff 76, the opacity patch 80 and/or inner cuff 72 and/or formation of the pocket 85 may be accomplished in accordance with the disclosure of commonly assigned U.S. Patent App. No. 62/134,622. The leg gasketing system 70 may comprise one or more longitudinally extending elastic members 55 as can be seen in FIG. 1. The pocket 85 may be free from elastics 55.

Opacity Strengthening Patch:

In some embodiments of the disposable absorbent articles detailed herein, an opacity strengthening patch 80 may be included as part of the chassis 20 as shown in FIG. 1. The opacity strengthening patch 80 is an additional layer of material. The opacity strengthening patch 80 may be connected to the leg gasketing system 70, the polymeric film layer, and/or the backsheet 26. The opacity strengthening patch 80 may be disposed between the backsheet 26 and leg gasketing system 70 in either the first waist region 14, the second waist region 18, or both the first waist region 14 and the second waist region 18 of the article; the opacity strengthening patch 80 may overlap at least one of the leg gasketing system 70 and/or the polymeric film layer (i.e., inner layer of the backsheet 26). The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the lateral edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis 20 where strength and opacity is desirable. Materials suitable to act as the opacity strengthening patch include materials having a basis weight of at least about 10 gsm, at least about 15 gsm, at least about 25 gsm. An opacity strengthening patch useful herein may exhibit the following tensile properties in the cross direction: at 2% engineering strain for a 1 inch wide sample, 0.4N; at 5% engineering strain for a 1 inch wide sample, 1.25N; at 10% engineering strain for a 1 inch wide sample, 2.5N. One opacity strengthening patch useful herein is available from Pegas, Znojmo, CZ, as supplier number 803968.

In one embodiment, the opacity strengthening patch 80 is discrete and is located in the front and back waist regions of the article. In one embodiment, the opacity strengthening patch is about 70 mm long in the front, optionally about 90 mm long in the front; optionally about 120 mm long in the front. In one embodiment, the opacity strengthening patch is about 70 mm long in the back, optionally about 100 mm long in the back, optionally about 140 mm long in the back. In one embodiment, the opacity strengthening patch is continuous and spans the entire length of the product.

In one embodiment, the opacity strengthening patch has a hunter color opacity of greater than about 15%, optionally greater than about 25%, optionally greater than about 40%, optionally greater than 60%.

In one embodiment the opacity strengthening patch is laterally outboard of the polymeric film layer. In one embodiment, the opacity strengthening patch overlaps the polymeric film layer in the lateral direction such that it can be affixed to the polymeric film in order to transmit laterally directed application and wearing forces from the opacity strengthening patch to the polymeric film layer. Any suitable bonding means known in the art may be used to affix the opacity strengthening patch to the polymeric film layer. In one embodiment, the opacity strengthening patch overlaps the polymeric film layer by about 5 mm, optionally about 10 mm, optionally about 15 mm, optionally about 20 mm, optionally less than about 30 mm.

In one embodiment, there is a lateral gap between the opacity strengthening patch and the polymeric film layer and the opacity strengthening patch is affixed by any suitable bonding means to the leg gasketing system, and the leg gasketing system is affixed to the polymeric film layer by any suitable bonding means such that application and wearing loads can transmit from the opacity strengthening patch to the gasketing system and then from the gasketing system to the polymeric film layer. In this embodiment, the gap is preferably less than 30 mm, more preferably less than 20 mm, more preferably less than 10 mm.

In one embodiment, there is a lateral gap between the opacity strengthening patch and the polymeric film layer; the opacity strengthening patch may be affixed by any suitable bonding means to the leg gasketing system and the body facing and garment facing sides of the leg gasketing system may be affixed together by any suitable bonding means so that the loads from the opacity strengthening patch are shared by both layers of the leg gasketing system. The leg gasketing system may be affixed to the polymeric film layer by any suitable bonding means such that application and wearing loads can transmit from the opacity strengthening patch to the leg gasketing system and then from the leg gasketing system to the polymeric film layer.

In one embodiment, the opacity strengthening patch overlaps the leg gasketing system in the lateral direction such that it can be affixed securely to the opacity strengthening patch layer by any suitable bonding means as a way to transmit application and wearing forces from the opacity strengthening patch to the leg gasketing system. In this embodiment, the opacity strengthening patch may overlap the leg gasketing system by about 5 mm, optionally about 10 mm, optionally less than about 15 mm, optionally less than about 25 mm.

In one embodiment the leg gasketing system has about the same lateral tensile strength properties as the opacity strengthening patch. In one embodiment the combined properties of the leg gasketing system and the backsheet nonwoven outer cover has about the same lateral tensile strength as the opacity strengthening patch. In another embodiment the outercover nonwoven has very low lateral strength between about 0% and about 10% engineering strain. In one embodiment, the outercover nonwoven may exhibit the following tensile properties: at 10% engineering strain for a 1 inch wide sample, 0.4N.

Construction Materials:

It is recognized that there are many combinations of material lateral tensile properties that could form a substantially suitable force transmission pathway in the waist region or the article without excessive lateral stretch in the waist region, and that the material force pathways may go from the opacity strengthening patch directly into the polymeric film layer or into the polymeric film layer through a variety of other layers in the region immediately outboard the polymeric film layer. These layers may include the topsheet, backsheet nonwoven, cuff, absorbent assembly, leg gasketing system, or any other layer that is located in a region adjacent to the polymeric film layer.

In one embodiment, the material of the leg gasketing system 70 is made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the present invention, the leg gasketing cuff 70 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example.

The leg gasketing cuff 70 may comprise a first nonwoven component layer comprising fibers having an average diameter in the range of about 8 microns to about 30 microns, a second nonwoven component layer comprising fibers having a number-average diameter of less than about 1 micron, a mass-average diameter of less than about 1.5 microns, and a ratio of the mass-average diameter to the number-average diameter less than about 2, and a third nonwoven component layer comprising fibers having an average diameter in the range of about 8 microns to about 30 microns. The second nonwoven component layer is disposed intermediate the first nonwoven component layer and the third nonwoven component layer.

The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxybutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calender bond process, for example, also called thermal point bonding.

In some embodiments, the use of an N-fiber layer in a nonwoven web may provide a low surface tension barrier that is as high as other nonwoven webs that have been treated with a hydrophobic coating or a hydrophobic melt-additive, and still maintain a low basis weight (e.g., less than 15 gsm or, alternatively, less than 13 gsm). The use of the N-fiber layer may also provide a soft and breathable (i.e., air permeable) nonwoven material that, at least in some embodiments, may be used in single web layer configurations in applications which previously used double web layer configurations. Furthermore, in some embodiments, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects (i.e., holes or pinholes through the mechanical bond site) created during the mechanical bonding process. N-fibers are further discussed in WO 2005/095700 and U.S. patent application Ser. No. 13/024,844.

In one embodiment, the inner cuff 72 web of material has a hydrostatic head of greater than about 2 mbar, greater than about 3 mbar, greater than about 4 mbar. In one embodiment, the outer cuff 76 web of material has a hydrostatic head of less than about 200 mbar, less than about 100 mbar, less than about 75 mbar, less than about 50 mbar, less than about 25 mbar, less than about 15 mbar.

In one embodiment, the folded outer cuff web of material has a basis weight of 10 gsm; optionally 13 gsm; optionally 15 gsm; optionally 18 gsm.

In one embodiment, the inner cuff 72 web of material has an opacity of from about 15% to about 50% hunter opacity; optionally from about 20% to about 45% hunter opacity. In one embodiment, the outer cuff 76 web of material has an opacity of from about 45% to about 75% hunter opacity; optionally from about 50% to about 70% hunter opacity; optionally less than about 75% hunter opacity; optionally less than about 70% hunter opacity.

In one embodiment, the inner cuff 72 web of material has an air permeability of less than about 50 $m^3/m^2/min$; optionally less than about 45 $m^3/m^2/min$. In one embodiment, the outer cuff 76 web of material has an air permeability of greater than about 5 $m^3/m^2/min$; optionally greater than about 10 $m^3/m^2/min$; optionally greater than about 15 $m^3/m^2/min$; optionally greater than about 20 $m^3/m^2/min$.

In one embodiment, the inner cuff 72 web of material has a WVTR of less than about 5500 $g/m^2/24$ hrs; optionally less than about 5400 $g/m^2/24$ hrs. In one embodiment, the outer cuff 76 web of material has a WVTR of greater than about 4250 $g/m^2/24$ hrs; optionally greater than about 4500 $g/m^2/24$ hrs; optionally greater than about 5000 $g/m^2/24$ hrs; optionally greater than about 5250 $g/m^2/24$ hrs; optionally greater than about 5500 $g/m^2/24$ hrs.

The gasketing cuffs 70 may be substantially inelastic or may be elastically extensible to dynamically fit at the wearer's leg. The gasketing cuff 70 may be formed by one or more elastic members 55 (such as elastic strands) operatively joined to the topsheet 24, backsheet 26, or any other suitable substrate used in the formation of the absorbent article 10. Suitable gasketing cuff construction is further described in U.S. Pat. No. 3,860,003

The inner cuff 72 may span the entire longitudinal length of the absorbent article 10. The inner cuff 72 may be formed by a flap and an elastic member 55 (such as elastic strands). The inner cuff 72 may be a continuous extension of any of the existing materials or elements that form the absorbent article 10.

The inner cuff 72 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap may comprise a nonwoven web such as spunbond webs, meltblown webs, carded webs, and combinations thereof (e.g., spunbond-meltblown composites and variants). Laminates of the aforementioned substrates may also be used to form the flap. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having inner cuffs and suitable construction of such cuffs may be found in U.S. Pat. Nos. 4,808,178 and 4,909,803. The elastic member 55 may span the longitudinal length of the inner cuff 72. In other embodiments, the elastic member 55 may span at least the longitudinal length of the inner cuff 72 within the crotch region 16. It is desirable that the elastic member 55 exhibits sufficient elasticity such that the inner cuff 72 remains in contact with the wearer during normal wear, thereby enhancing the barrier properties of the inner cuff 72. The elastic member 55 may be connected to the flap at opposing longitudinal ends. In certain embodiments, the flap may be folded over onto itself so as to encircle the elastic member 55.

The inner cuff 72 and/or outer cuff 76 may be treated, in full or in part, with a lotion, as described above with regard to topsheets, or may be fully or partially coated with a hydrophobic surface coating as detailed in U.S. application Ser. No. 11/055,743, which was filed Feb. 10, 2005. Hydrophobic surface coatings usefully herein may include a non-aqueous, solventless, multicomponent silicone composition. The silicone composition includes at least one silicone polymer and is substantially free of aminosilicones. A particularly suitable hydrophobic surface coating is available from Dow Corning Mich., Salzburg as supplier code 0010024820.

and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 13:
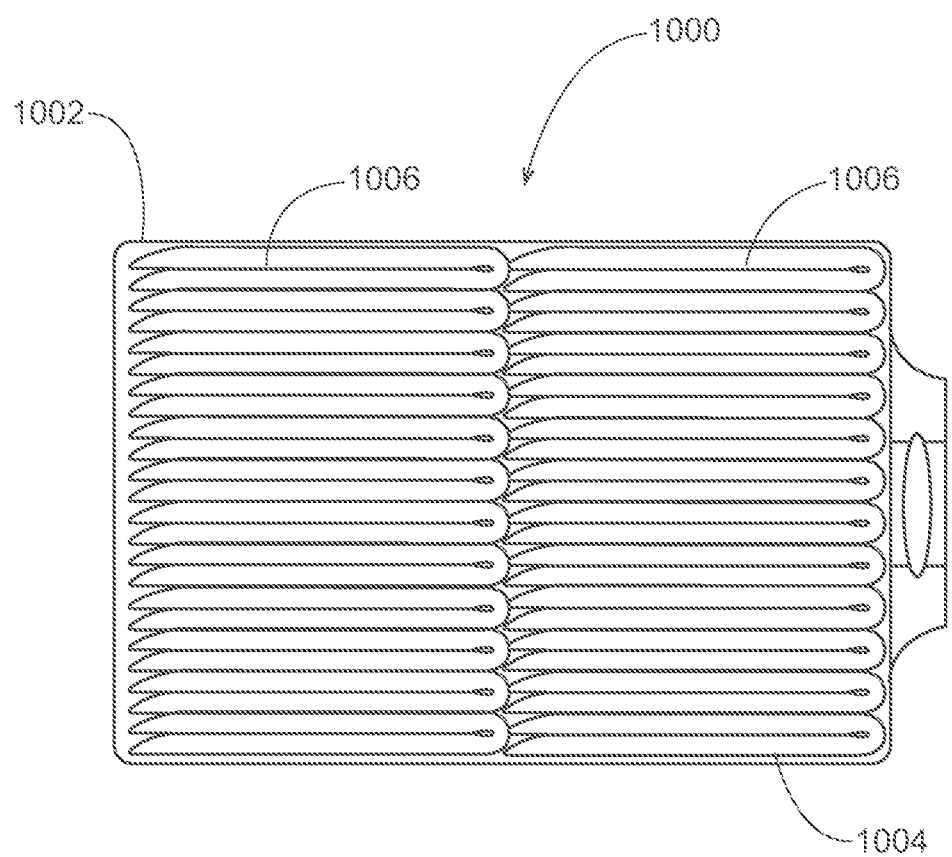
FIG. 13 is a schematic side elevation view of a package in accordance with one embodiment of the present invention.

FIG. 13 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Examples

| Product | Lot No. | Opacity % | | Air Permeability m³/m²/min | | WVTR g/m²/24 hrs | | Hydrohead mbar | | 32 dyne Strikethrough Sec | |
|---|---|---|---|---|---|---|---|---|---|---|---|
| | | Outer Cuff | Inner Cuff | Outer Cuff | Inner Cuff | Outer Cuff | Inner Cuff | Outer Cuff | Inner Cuff | Outer Cuff | Inner Cuff |
| Prototype N-Fiber | NA | 58.7 ± 2.2 | 37.6 ± 3.2 | 26.8 ± 5.6 | 36.9 ± 4.6 | 5905 ± 129 | 5224 ± 87 | 16.8 ± 2.1 | 12.3 ± 1.3 | 21.0 ± 3.5 | 9.2 ± 1.5 |
| Prototype SMS | NA | 65.8 ± 1.8 | 39.0 ± 1.0 | 65.6 ± 11.5 | 38.5 ± 3.8 | 5748 ± 276 | 5193 ± 145 | 16.3 ± 1.8 | 10.0 ± 1.7 | 15.6 ± 1.9 | 7.6 ± 1.4 |
| Pampers BabyDry | 0089U 01139 0422 | 80.1 ± 0.4 | 38.8 ± 3.8 | 2.1 ± 1.0 | 56.1 ± 6.3 | 4063 ± 67 | 5252 ± 157 | >200 | 6.7 ± 0.8 | >100 | 10.1 ± 0.5 |
| Luvs | 1047U 01139 0518 | 85.3 ± 1.2 | 36.4 ± 3.4 | 3.1 ± 1.9 | 90.2 ± 9.3 | 304 ± 144 | 5244 ± 26 | >200 | 6.5 ± 1.0 | >100 | 11.8 ± 1.4 |
| Huggies Little Movers | BI006 912B | 80.1 ± 1.0 | 45.4 ± 4.2 | 2.6 ± 0.4 | 45.0 ± 15.7 | 3673 ± 190 | 5581 ± 90 | >200 | 8.3 ± 1.3 | >100 | 14.3 ± 3.5 |
| Huggies Supreme | NM12 75U1F 0755 | 72.7 ± 2.2 | 53.6 ± 2.3 | 4.4 ± 1.1 | 145.2 ± 23.2 | 375 ± 77 | 5688 ± 85 | >200 | 9.2 ± 1.8 | >100 | 14.6 ± 3.1 |

Results are expressed as the average ± one standard deviation
Prototype N-Fiber is a 13 gsm SMNS available from Polymer Group Inc
Prototype SMS is a 15 gsm SMS (Spunbonded-Meltblown-Spunbonded) nonwoven available from Fibertex under the Comfort Line Package The absorbent articles 10 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges Combination of Embodiments While embodiments are described separately herein for brevity and clarity, combinations of the various embodiments are contemplated and within the scope of the present disclosure.

A. An absorbent article for wearing about the lower torso of a wearer, the absorbent article comprising:

a first waist region having a first waist edge, a second waist region having a second waist edge, a crotch region disposed between the first and second waist regions; and a first longitudinal edge and a second longitudinal edge;

a chassis comprising a topsheet, a backsheet, and an absorbent core disposed between the topsheet and backsheet; and a waist gasketing element joined to the chassis and disposed in one of the first waist region or the second waist region, the waist gasketing element having a top layer and a bottom layer, an inboard lateral edge and an outboard lateral edge; and wherein the waist gasketing element further comprises a first area, A1;

a closure bond region, wherein the top layer is bonded to the bottom layer in the closure bond region by a closure bonding technique and wherein the closure bond region comprises an aggregate closure bond area, BA, wherein the aggregate closure bond area, BA, is at least about 10% of the first area, A1.

B. The absorbent article of paragraph A wherein the top layer and/or the bottom layer comprises one of the group of a nonwoven, a film, a laminate and combinations thereof.

C. The absorbent article of any of paragraphs A or B wherein the closure bonding technique comprises one of the group of adhesive bonding, ultrasonic bonding, mechanical bonding and combinations thereof.

D. The absorbent article of paragraph C wherein the closure bond region comprises a continuous closure bond.

E. The absorbent article of any of the preceding paragraphs wherein the closure bond region comprises discrete closure bonds.

F. The absorbent article of any of the preceding paragraphs wherein the aggregate bond area, BA, is less than about 90% of the first area A1.

G. The absorbent article of any of the preceding paragraphs wherein the top layer and bottom layer are formed by a single web of material.

H. The absorbent article of any of the preceding paragraphs wherein the waist gasketing element comprises:
one or more elastic members joined to the top and/or bottom layer by an elastic bonding technique, and
an aggregate elastic bond area, EA,
wherein the aggregate elastic bond area, EA, is less than the aggregate closure bond area, BA.

I. The absorbent article of paragraph H wherein the elastic bonding technique comprises one of the group of strand coating, spiral coating, or combinations thereof.

J. The absorbent article of any of paragraphs H-I wherein the aggregate elastic bond area is about 30% of the first area, A1, or less.

K. The absorbent article of any of paragraphs H-J wherein the closure bonding technique and the elastic bonding technique are different.

L. The absorbent article of any of paragraphs H-L wherein one or more closure bonds encase at least one elastic member.

M. The absorbent article of any of the preceding paragraphs wherein the outboard lateral edge is at least partially coterminous with the waist edge of the one of the first or the second waist regions.

N. The absorbent article of any of the preceding paragraphs wherein the closure bond region is at least partially disposed on the outboard lateral edge.

O. The absorbent article of any of the preceding paragraphs further comprising a second waist gasketing element disposed in the other of the first or the second waist regions.

P. The absorbent article of paragraph O wherein the second waist gasketing element comprises a top layer and a bottom layer, and a second closure bond region disposed in the second waist gasketing element, wherein the top layer of the second waist gasketing element is bonded to the bottom layer of the second waist gasketing element in the second closure bond region.

Q. The absorbent article of paragraph P wherein the top layer and bottom layer of the second waist element formed by a single web of material.

R. The absorbent article of paragraphs O or P wherein:
the first waist gasketing element comprises a first outboard lateral edge that is at least partially coterminous with the first waist edge, the first outboard lateral edge comprising a first width, W1; and
the second waist gasketing element comprises a second outboard lateral edge that is at least partially coterminous with the second waist edge, the second outboard lateral edge comprising a second width, W2; and
W2 is substantially the same as W1.

S. The absorbent article of any of paragraphs P-R wherein the first closure bond region comprises a first closure bonding technique and the second closure bond region comprises a second closure bonding technique; and wherein the first and second bonding techniques are the same.

T. The absorbent article of any of paragraphs P-R wherein the first closure bond region comprises a first closure bonding technique and the second closure bond region comprises a second closure bonding technique; and wherein the first and second bonding techniques differ by one of the group consisting of bond type, bonding material, bond area, bond strength, bond shape, and/or bond size.

U. A package comprising a plurality of the absorbent articles of any of the preceding paragraphs, wherein the package has an In-Bag Stack Height in the range of about 70 mm to about 100 mm, according to the In-Bag Stack Height Test herein.

V. An absorbent article for wearing about the lower torso of a wearer, the absorbent article comprising:
a first waist region having a first waist edge, a second waist region having a second waist edge, a crotch region disposed between the first and second waist regions; and a first longitudinal edge and a second longitudinal edge;
a chassis comprising a topsheet, a backsheet, and an absorbent core disposed between the topsheet and backsheet; and
a waist gasketing element joined to the chassis and disposed in the first or second waist region, the waist gasketing element having a top layer and a bottom layer, an outboard lateral edge and an inboard lateral edge, wherein the waist gasketing element comprises two or more bonding techniques.

W. The absorbent article of paragraph V wherein the two or more bonding techniques comprise at least two of the group consisting of: adhesive bonds, ultrasonic bonds, and mechanical bonds.

X. The absorbent article of paragraphs V or W wherein the two or more bonding techniques comprise a first adhesive bond and a second adhesive bond, wherein the first and second adhesive bonds differ by one of the group consisting of: adhesive material, area, length, width, bond strength, bond shape, and combinations thereof.

Y. The absorbent article of any of paragraphs V-X wherein at least two of the two or more bonding techniques overlap another.

Z. The absorbent article of any of paragraphs V-Y wherein the two or more bonding techniques are disposed between the top and bottom layers.

AA. A method of forming front and back waist gasketing elements on an absorbent article comprising the steps of:
providing a web of chassis material;
providing a plurality of waist gasketing elements, each waist gasketing element having a first transverse edge and a second transverse edge; and wherein each waist gasketing element further comprises a top layer and a bottom layer;
bonding the top and bottom layers of the waist gasketing elements in closure bond regions;

joining the waist gasketing elements to the web of chassis material to form a strip of final articles;

dividing the strip of final articles between the first and second transverse edges of the waist gasketing elements such that a cut separates two final articles, the two final articles comprising a leading article and a trailing article, wherein each cut:

is disposed at least partially within a closure bond region;

forms a back waist edge of the leading article and a front waist edge of the trailing article; and forms an outboard lateral edge of a back waist gasketing element on the leading article and an outboard lateral edge of a front waist gasketing element on the trailing article.

BB. The method of paragraph AA wherein bonding the top and bottom layers further comprises bonding by one of the group consisting of adhesive bonding, ultrasonic bonding, mechanical bonding and combinations thereof.

CC. The method of paragraphs AA or BB wherein the top layer and bottom layer of at least one of the plurality of waist gasketing elements is formed from a single web of material.

DD. The method of any of paragraphs AA-CC wherein the bonding step comprises continuously bonding the top and bottom layers.

EE. The method of any of paragraphs AA-CC wherein the bonding step comprises intermittently bonding the top and bottom layers.

FF. The method of any of paragraphs AA-EE wherein the bonding step comprises two or more bonding techniques.

GG. The method of any of paragraphs AA-FF further comprising providing a web of waist gasketing material; folding the web of waist gasketing material to form the top and bottom layer of at least one of the waist gasketing elements.

Test Methods:

Opacity Method

Opacity is measured using a 0° illumination/45° detection, circumferential optical geometry, spectrophotometer with a computer interface such as the HunterLab LabScan XE running Universal Software (available from Hunter Associates Laboratory Inc., Reston, Va.) or equivalent instrument. Instrument calibration and measurements are made using the standard white and black calibration plates provided by the vendor. All testing is performed in a room maintained at 23±2° C. and 50±2% relative humidity.

The spectrophotometer is conFig.d for the XYZ color scale, D65 illuminant, 10° standard observer, with UV filter set to nominal. The instrument is standardized according to the manufacturer's procedures using the 0.7 inch port size and 0.5 inch area view. After calibration, the software is set to the Y opacity procedure which prompts the operator to cover the sample with either the white or black calibration tile during the measurement.

Articles are pre-conditioned at 23° C.±2° C. and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is placed over the measurement port. The specimen should completely cover the port with the surface corresponding to the inner-facing surface of the cuff directed toward the port. The specimen is gently extended until taut in its longitudinal direction so that the cuff lies flat against the port plate. Adhesive tape is applied to secure the cuff to the port plate in its extended state for testing. Tape should not cover any portion of the measurement port. The specimen is then covered with the white standard plate. A reading is taken, then the white tile is removed and replaced with the black standard tile without moving the specimen. A second reading is taken, and the opacity is calculated as follows:

$$\text{Opacity} = (Y\text{value}_{(black\ backing)} / Y\text{value}_{(white\ backing)}) \times 100$$

Specimens from five identical articles (10 inner cuff (5 left and 5 right) and 10 outer cuff (5 left and 5 right)) are analyzed and their opacity results recorded. The average opacity for the inner cuffs and the outer cuffs are calculated and report separately, each to the nearest 0.01%.

Water Vapor Transmission Rate Method

Water Vapor Transmission Rate (WVTR) is measured using the wet cup approach. A cylindrical cup is filled with water, maintaining a constant headspace between the water surface and a specimen sealed over the cup's upper opening. The vapor loss is measured gravimetrically after heating the assembled cup for a specified time in an oven. All testing is performed in a room maintained at 23° C.±2° C. and 50%±2% relative humidity.

Articles are preconditioned at 23° C.±2° C. and 50%±2% relative humidity for two hours prior to testing. The article stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens from the cuffs on the right side of the article are prepared.

Glass straight walled, cylindrical vials, 95 mm tall with a 17.8 mm internal diameter at the opening are used as WVTR test vials. Each test vial is filled with distilled water accurately to a level 25.0 mm±0.1 mm from the upper lip of the vial's opening. The specimen is placed, inner-facing surface of the cuff downward, over the vial's opening. The specimen is gently pulled taut and secured around the vial's circumference with an elastic band. The specimen is further sealed by wrapping Teflon tape around the vial's circumference. A preferred Teflon tape is a thread sealant tape 0.25" wide available from McMaster Carr (cat. No. 4591K11) or equivalent. The Teflon tape is applied up to the top edge of the vial but should not cover any portion of the vial's opening. The mass of the vial assembly (vial+specimen+sealing tape) is weighed to the nearest 0.0001 gram. This is the starting mass.

The vial assemblies are placed upright in a mechanical convection oven (e.g. Lindberg/BlueM oven available from ThermoScientific or equivalent) maintained at 38±1° C. for 24 hours, taking care to avoid contact between the water in the vials and the specimens. After 24 hours has elapsed, the vial assemblies are removed from the oven and allowed to come to room temperature. The mass of each vial assembly is measured to the nearest 0.0001 gram. This is the final mass.

The WVTR is calculated using the following equation:

WVTR (g/m²/24 hrs)=([starting mass (g)−final mass (g)]/surface area (m²))/24 hrs Specimens from five identical articles (10 inner cuff (5 left and 5 right) and 10 outer cuff (5 left and 5 right)) are analyzed and their WVTR results recorded. The average WVTR for the inner cuffs and the outer cuffs are each reported separately to the nearest 1 g/m²/24 hrs.

Air Permeability Test

Air permeability is tested using a TexTest FX3300 Air Permeability Tester (available from Advanced Testing Instruments, Greer, S.C.) with a custom made 1 cm² circular aperture (also available from Advanced Testing Instruments) or equivalent instrument. The instrument is calibrated according to the manufacturer's procedures. All testing is performed in a room maintained at 23° C.±2° C. and 50%±2% relative humidity.

The articles are pre-conditioned at 23° C.±2° C. and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is centered over the measurement port. The specimen should completely cover the port with the surface corresponding to the inward-facing surface of the cuff directed toward the port. The specimen is gently extended in its longitudinal direction until taut so that the cuff lies flat across the port. Adhesive tape is applied to secure the cuff across the port in its extended state for testing. Tape should not cover any portion of the measurement port. The test pressure is set to allow air to pass through the specimen. For non-woven cuffs the pressure is typically set for 125 Pa and for cuffs containing films typically 2125 Pa is used. The sample ring is closed and the measuring range is adjusted until the range indicator shows green to indicate that the measurement is within the accepted limits of the instrument. The air permeability is recorded to the nearest 0.1 m³/m²/min.

Hydrostatic Head Test

Hydrostatic head is tested using a TexTest FX3000 Hydrostatic Head Tester (available from Advanced Testing Instruments, Greer, S.C.) with a custom made 1.5 cm² circular measurement port (also available from Advanced Testing Instruments). Two annular sleeve rings, the same dimensions as the gaskets around the measurement ports, are cut from the standard protective sleeves for fine nonwovens (part FX3000-NWH, available from Advanced Testing Instruments). The sleeve rings are then adhered with two-sided adhesive tape to the sample facing surfaces of the upper and lower gaskets of the TexTest instrument to protect the specimen during clamping. Standardize the instrument according to the manufacturer's procedures. All testing is performed in a room maintained at about 23° C.±2° C. and about 50%±2% relative humidity.

Precondition the articles at about 23° C.±2° C. and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the upper test head. The specimen should completely cover the port with the surface corresponding to the outward-facing surface of the cuff directed toward the port (inner-facing surface will then be facing the water). Gently extend the specimen taut in its longitudinal direction so that the cuff lies flat against the upper test plate. Adhesive tape is applied to secure the cuff to the test plate in its extended state for testing. Tape should not cover any portion of the measurement port.

Fill the TexTest syringe with distilled water, adding the water through the measurement port of the lower test plate. The water level should be filled to the top of the lower gasket. Mount the upper test head onto the instrument and lower the test head to make a seal around the specimen. The test speed is set to 3 mbar/min for samples that have a hydrostatic head of 50 mbar or less and a speed of 60 mbar/min for samples with a hydrostatic head above 50 mbar. Start the test and observe the specimen surface to detect water droplets penetrating the surface. The test is terminated when one drop is detected on the surface of the specimen or the pressure exceeds 200 mbar. Record the pressure to the nearest 0.5 mbar or record as >200 mbar if there was no penetration detected.

A total of five identical articles (10 inner cuff and 10 outer cuff specimens) are analyzed and their hydrostatic head results recorded. Calculate and report the average hydrostatic head for the inner cuffs and the outer cuffs and report each to the nearest 0.1 mbar.

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad.

For this test, the reference absorbent pad is 5 plies of Ahlstrom grade 989 filter paper (10 cm×10 cm) and the test fluid is a 32 mN/m low surface tension fluid.

This test is designed to characterize the low surface tension fluid strikethrough performance (in seconds) of webs intended to provide a barrier to low surface tension fluids, such as runny BM, for example.

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strike-through time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

All testing is performed in a room maintained at about 23° C.±2° C. and about 50%±2% relative humidity. The Ahlstrom filter paper and test articles are conditioned in this controlled environment for 24 hours and 2 hours before testing.

All testing is performed in a room maintained at about 23° C.±2° C. and about 50%±2% relative humidity. The Ahlstrom filter paper and test articles are conditioned in this controlled environment for 24 hours and 2 hours before testing Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Precondition the test articles at about 23° C.±2° C. and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the strike through plate. The specimen should completely cover the port with the surface corresponding to the body-facing surface of the cuff directed toward the port. Gently extend the specimen taut in its longitudinal direction so that the cuff lies flat against the upper test plate. Adhesive tape is applied to secure the cuff to the test plate in its extended state for testing. Tape should not cover any portion of the measurement port.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for three articles. Average the six values and report as the 32 mN/m low surface tension strikethrough time to the nearest 0.1 seconds.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 13). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for wearing about the lower torso of a wearer, the absorbent article comprising:

a first waist region having a first waist edge, a second waist region having a second waist edge, a crotch region disposed between the first and second waist regions; and a first longitudinal edge and a second longitudinal edge;

a chassis comprising a topsheet, a backsheet, and an absorbent core disposed between the topsheet and backsheet; and a waist gasketing element joined to the chassis and disposed in one of the first waist region or the second waist region, the waist gasketing element having a top layer and a bottom layer, an inboard lateral edge and an outboard lateral edge; and wherein the waist gasketing element further comprises a first area, A1;

a closure bond region, wherein the top layer is bonded to the bottom layer in the closure bond region by one or more closure bonds and wherein the closure bond region comprises an aggregate closure bond area, BA, wherein the aggregate closure bond area, BA, is at least 10% of the first area, A1.

2. The absorbent article of claim 1 wherein the top layer and/or the bottom layer comprises one of the group of a nonwoven, a film, a laminate and combinations thereof.

3. The absorbent article of claim 1 wherein the closure bonds are formed by a closure bonding technique comprising one of the group of adhesive bonding, ultrasonic bonding, mechanical bonding and combinations thereof.

4. The absorbent article of claim 1 wherein the closure bond region comprises a single closure bond is in the form of a continuous bar.

5. The absorbent article of claim 1 wherein the closure bond region comprises a plurality of discrete closure bonds.

6. The absorbent article of claim 1 wherein the chassis is attached to the waist gasketing element in the closure bond region.

7. The absorbent article of claim 1 wherein the top layer and bottom layer are formed by a single web of material.

8. The absorbent article of claim 1 wherein the waist gasketing element comprises:

one or more elastic members joined to the top and/or bottom layer by an elastic bonding technique, and an aggregate elastic bond area, EA, wherein the aggregate elastic bond area, EA, is less than the aggregate closure bond area, BA.

9. The absorbent article of claim 8 wherein the aggregate elastic bond area is about 30% of the first area, A1, or less.

10. The absorbent article of claim 8 wherein the closure bonding technique and the elastic bonding technique are different.

11. The absorbent article of claim 8 wherein at least one closure bond encases at least one elastic member.

12. The absorbent article of claim 1 wherein the outboard lateral edge is at least partially coterminous with the waist edge of the one of the first or the second waist regions.

13. The absorbent article of claim 1 wherein the closure bond region is at least partially disposed on the outboard lateral edge.

14. The absorbent article of claim 1 wherein the closure bond is an adhesive bond having a basis weight of from about 3 gsm to about 10 gsm.

15. An absorbent article for wearing about the lower torso of a wearer, the absorbent article comprising:

a first waist region having a first waist edge, a second waist region having a second waist edge, a crotch region disposed between the first and second waist regions; and a first longitudinal edge and a second longitudinal edge;

a chassis comprising a topsheet, a backsheet, and an absorbent core disposed between the topsheet and backsheet; and a first waist gasketing element joined to the chassis and disposed in the first waist region, the first waist gasketing element having a top layer and a bottom layer;

a first closure bond region disposed in the first waist gasketing element, wherein the top layer is bonded to the bottom layer in the first closure bond region, wherein the first waist gasketing element comprises one or more elastic members joined to the top and/or bottom layer by one or more elastic bonds, wherein the first closure bond region comprises a closure bonding technique and the one or more elastic bonds comprise an elastic bonding technique, wherein the closure bonding technique and the elastic bonding technique are different;

a second waist gasketing element joined to the chassis disposed in the second waist region, the second waist gasketing element having a top layer and a bottom layer; and a second closure bond region disposed in the second waist gasketing element, wherein the top layer of the second waist gasketing element is bonded to the bottom layer of the second waist gasketing element in the second closure bond region.

16. The absorbent article of claim 15 wherein:

the first waist gasketing element comprises a first outboard lateral edge that is at least partially coterminous with the first waist edge, the first outboard lateral edge comprising a first width, W1;

the second waist gasketing element comprises a second outboard lateral edge that is at least partially coterminous with the second waist edge, the second outboard lateral edge comprising a second width, W2; and W2 is substantially the same as W1.

17. An absorbent article for wearing about the lower torso of a wearer, the absorbent article comprising:
- a first waist region having a first waist edge, a second waist region having a second waist edge, a crotch region disposed between the first and second waist regions; and a first longitudinal edge and a second longitudinal edge;
- a chassis comprising a topsheet, a backsheet, and an absorbent core disposed between the topsheet and backsheet; and
- a waist gasketing element joined to the chassis and disposed in the first or second waist region, the waist gasketing element comprising a top layer, a bottom layer, an outboard lateral edge, an inboard lateral edge, a closure bond region in which the top layer is bonded to the bottom layer, and one or more elastic members joined to the top and/or bottom layer by one or more elastic bonds, wherein the closure bond region comprises a closure bonding technique and the one or more elastic bonds comprise an elastic bonding technique, and wherein the closure bonding technique and the elastic bonding technique are different.

18. The absorbent article of claim 17 wherein the closure bond region at least partially overlaps the one or more elastic bonds.

19. The absorbent article of claim 17 wherein the closure bonding technique comprises one of th group of adhesive bonding, ultrasonic bonding, mechanical bonding, and combinations thereof.

20. The absorbent article of claim 17 wherein the outboard lateral edge of the waist gasketing element is at least partially coterminous with the waist edge of the first or the second waist regions.

21. The absorbent article of claim 17 wherein the closure bond region is at least partially disposed on the outboard lateral edge.

* * * * *